(12) United States Patent
Rusk et al.

(10) Patent No.: US 9,393,137 B2
(45) Date of Patent: Jul. 19, 2016

(54) METHOD FOR LOADING A STENT INTO A DELIVERY SYSTEM

(75) Inventors: Emily E. Rusk, Boston, MA (US); Stephan Mangin, Austin, TX (US); Claude O. Clerc, Marlborough, MA (US); Michael Zupkofska, Rockland, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1237 days.

(21) Appl. No.: 11/860,075

(22) Filed: Sep. 24, 2007

(65) Prior Publication Data

US 2009/0082840 A1 Mar. 26, 2009

(51) Int. Cl.
*A61F 2/06* (2013.01)
*A61F 2/95* (2013.01)

(52) U.S. Cl.
CPC ........... *A61F 2/95* (2013.01); *A61F 2002/9505* (2013.01); *A61F 2002/9522* (2013.01); *A61F 2250/006* (2013.01); *A61F 2250/0091* (2013.01); *A61F 2250/0097* (2013.01)

(58) Field of Classification Search
CPC ... A61F 2/95; A61F 2/962; A61F 2002/9505; A61F 2002/9517; A61F 2002/9522; A61F 2250/0097; A61F 2250/006
USPC ...................... 623/1.11, 1.12, 1.15
See application file for complete search history.

(56) References Cited

U.S. PATENT DOCUMENTS

| | | | |
|---|---|---|---|
| 4,503,569 A | 3/1985 | Dotter | |
| 4,580,568 A * | 4/1986 | Gianturco | A61F 2/86 138/97 |
| 4,732,152 A | 3/1988 | Wallstén et al. | |
| 4,830,003 A * | 5/1989 | Wolff | A61F 2/86 606/191 |
| 4,856,516 A | 8/1989 | Hillstead | |
| 5,026,377 A | 6/1991 | Burton et al. | |
| 5,484,444 A | 1/1996 | Braunschweilr et al. | |
| 5,653,746 A | 8/1997 | Schmitt | |
| 5,876,448 A | 3/1999 | Thompson et al. | |
| 6,099,562 A | 8/2000 | Ding et al. | |
| 6,162,244 A | 12/2000 | Braun et al. | |
| 6,251,132 B1 * | 6/2001 | Ravenscroft et al. | 623/1.11 |
| 6,322,586 B1 * | 11/2001 | Monroe et al. | 623/1.11 |
| 6,325,822 B1 | 12/2001 | Chouinard et al. | |
| 6,350,278 B1 | 2/2002 | Lenker et al. | |
| 6,540,773 B2 | 4/2003 | Dong | |
| 6,554,855 B1 | 4/2003 | Dong | |
| 6,585,758 B1 | 7/2003 | Chouinard et al. | |

(Continued)

FOREIGN PATENT DOCUMENTS

EP 0596145 A1 5/1994
EP 1690512 A1 8/2006

(Continued)

OTHER PUBLICATIONS

Search Report for PCT/US2008/077478 dated Dec. 12, 2008.

(Continued)

*Primary Examiner* — Katherine Rodjom
(74) *Attorney, Agent, or Firm* — Seager, Tufte & Wickhem, LLP

(57) ABSTRACT

Methods for assembling a stent delivery system are provided, as well as the stent delivery assemblies and devices formed by such methods. Also provided is a method for loading a stent into a delivery system.

22 Claims, 18 Drawing Sheets

(56) References Cited

U.S. PATENT DOCUMENTS

| | | | |
|---|---|---|---|
| 6,592,548 B2 * | 7/2003 | Jayaraman | 604/103.04 |
| 6,592,549 B2 | 7/2003 | Gerdts et al. | |
| 6,626,936 B2 | 9/2003 | Stinson | |
| 7,083,641 B2 * | 8/2006 | Stinson et al. | 623/1.34 |
| 2002/0013599 A1 * | 1/2002 | Limon | A61F 2/95 606/191 |
| 2002/0035396 A1 * | 3/2002 | Heath | 623/1.15 |
| 2002/0198586 A1 | 12/2002 | Inoue | |
| 2003/0204241 A1 | 10/2003 | Dong | |
| 2004/0204749 A1 | 10/2004 | Gunderson | |
| 2005/0049682 A1 | 3/2005 | Leanna et al. | |
| 2005/0149164 A1 | 7/2005 | Rivelli, Jr. | |
| 2005/0256563 A1 | 11/2005 | Clerc et al. | |
| 2006/0116752 A1 | 6/2006 | Norton et al. | |
| 2006/0142852 A1 | 6/2006 | Sowinski et al. | |
| 2006/0190075 A1 | 8/2006 | Jordan et al. | |
| 2006/0276887 A1 | 12/2006 | Brady et al. | |
| 2007/0208409 A1 | 9/2007 | Quigley | |
| 2007/0270931 A1 | 11/2007 | Leanna et al. | |
| 2007/0270932 A1 * | 11/2007 | Headley et al. | 623/1.11 |
| 2007/0270937 A1 | 11/2007 | Leanna | |
| 2008/0021538 A1 * | 1/2008 | Wright et al. | 623/1.12 |
| 2008/0243106 A1 * | 10/2008 | Coe et al. | 606/1 |

FOREIGN PATENT DOCUMENTS

| | | |
|---|---|---|
| FR | 2902641 A1 | 12/2007 |
| WO | 2007081940 A2 | 7/2007 |

OTHER PUBLICATIONS

English-Language Abstract of EP 0596145 (A1).
English-Language Abstract of FR 2902641 (A1).

* cited by examiner

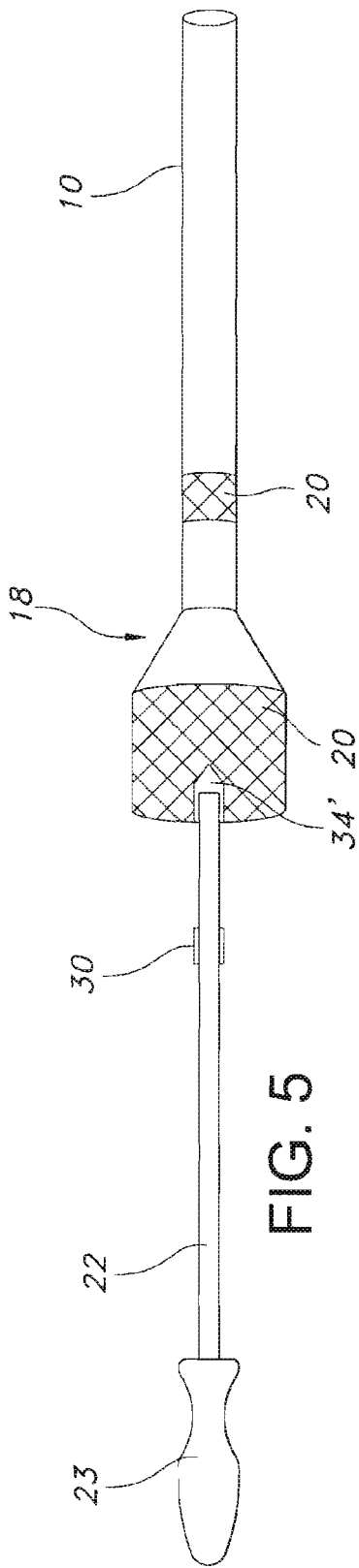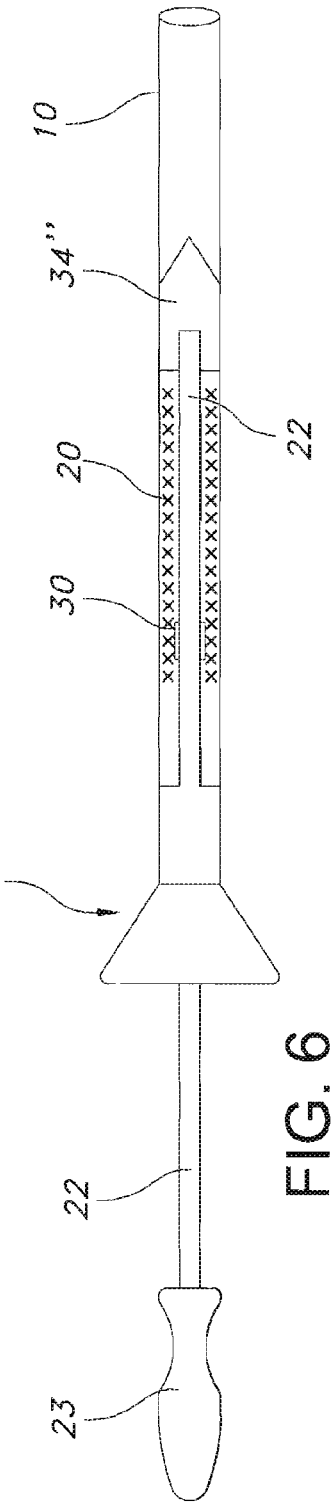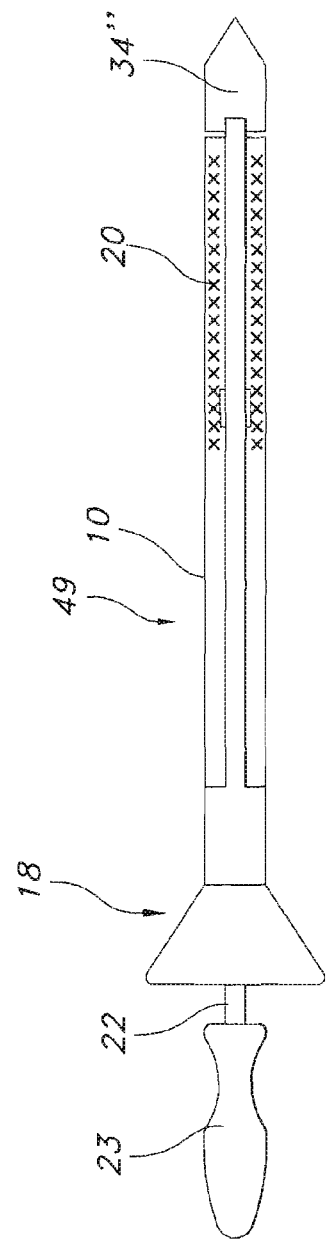

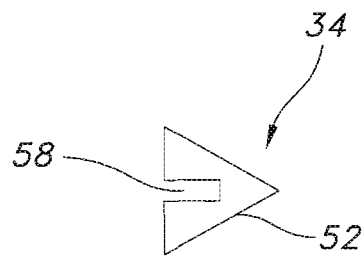
FIG. 35A
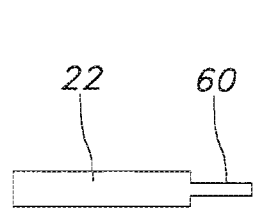 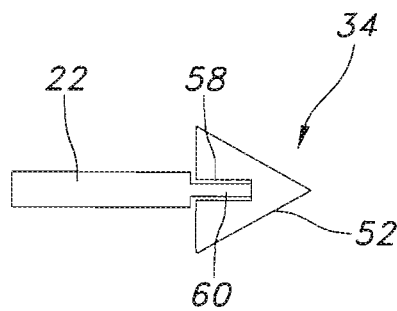
FIG. 35B  FIG. 35C
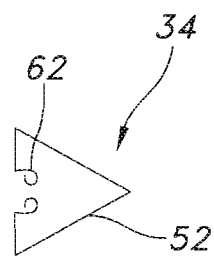 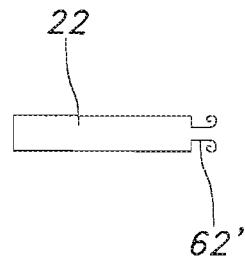
FIG. 36A  FIG. 36B
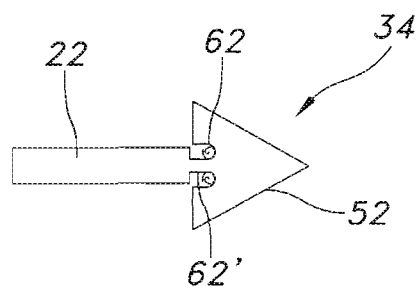
FIG. 36C

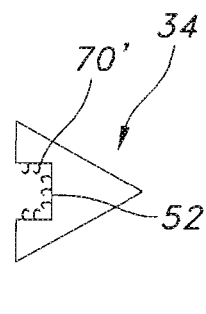
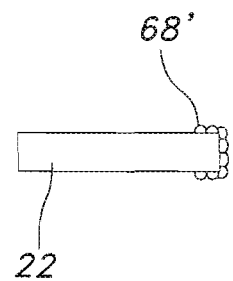
FIG. 39A    FIG. 39B
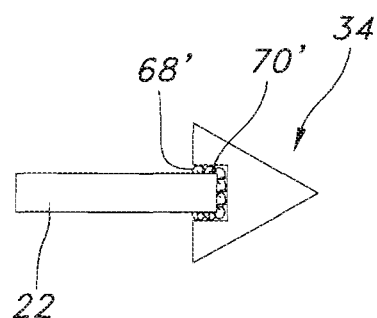
FIG. 39C

METHOD FOR LOADING A STENT INTO A DELIVERY SYSTEM

FIELD OF THE INVENTION

This invention relates to methods for assembling a stent delivery system, as well as to stent delivery assemblies and devices. This invention also relates to a method for loading a stent into a stent delivery system.

BACKGROUND OF THE INVENTION

Stent delivery systems are well-known in the art. The assembly of such delivery systems, however, often may be complicated. In particular, although it is common practice to load a stent into a sheath during assembly of a stent delivery system, such loading often involves numerous steps and often requires the use of multiple components (e.g., tools and fixtures) that are not part of the stent delivery system. For example, currently available stent delivery systems often require that a stent be loaded onto a delivery system by means of a funnel, basket or other similar device. However, it is often difficult and/or time-consuming to assemble a stent onto a delivery system by such means. Accordingly, there is a need for simplified methods of loading a stent into stent delivery systems during assembly of the same.

SUMMARY OF THE INVENTION

The present invention is directed to methods for inserting a stent into a stent delivery system, as well as to stent delivery systems and devices. In particular, the present invention relates to positioning a stent within a tubular structure by means of another tubular structure for the purpose of deploying the stent in a body. Moreover, the present invention relates to the resultant assemblies and devices formed by positioning a stent within a tubular structure in such a manner.

In one aspect of the invention, there is provided a device for delivering a stent to a patient for implantation including: (i) a first tubular structure having a proximal end, a distal end, and a lumen extending therethrough; (ii) a second tubular structure having a proximal end, a distal end, and a lumen extending therethrough; (iii) a distensible stent having a proximal end and a distal end; and (iv) a means for moving the stent. In such embodiments, the stent may be disengagedly coupled to the inner tubular structure by means of the means for moving the stent.

In another aspect of the invention, there is provided a stent delivery system which includes a device for delivering a stent to a patient for implantation including: (i) a first tubular structure having a proximal end, a distal end, and a lumen extending therethrough; (ii) a second tubular structure having a proximal end, a distal end, and a lumen extending therethrough; (iii) a distensible stent having a proximal end and a distal end; and (iv) a means for moving the stent. In such embodiments, the stent may be disengagedly coupled to the inner tubular structure by means of the means for moving the stent. In another aspect of the invention, there is provided a method for assembling a stent delivery system including: (i) providing (a) a first tubular structure having a proximal end, a distal end, and a lumen extending therethrough; (b) a second tubular structure having a proximal end, a distal end, a stent-engaging portion, and a lumen extending therethrough; and (c) a distensible stent having a proximal end and a distal end; (ii) inserting a portion of the stent into the proximal end of the first tubular structure, wherein the portion of the stent is in a constrained state relative to a portion of the stent that is not inserted into the first tubular structure; and (iii) inserting the second tubular structure into the proximal end of the first tubular structure to cause the stent-engaging portion to engage the stent such that relative movement of the second tubular structure causes relative movement of the stent.

In yet another aspect of the invention, there is provided a method for loading a stent into a sheath delivery system including the steps of: (i) providing a sheath delivery system including at least one first tubular structure having a proximal end and a distal end; wherein said proximal end of said tubular structure has a handle attached thereto and wherein said tubular structure includes a visual marker thereon; (ii) providing a distensible stent having a distal end, a proximal end, and a lumen extending therethrough; (iii) providing a second tubular structure having a proximal end, a distal end, a stent-engaging portion, and a lumen extending therethrough; (iv) passing the stent through the handle and into the tubular structure of the sheath delivery system until the distal end of the stent is aligned with the visual marker and such that a portion of the stent is partially constrained within the tubular structure; and (v) passing a second tubular structure into the lumen of the stent such that the second tubular structure becomes releasably engaged to the stent, wherein movement of the second tubular structure toward the distal end of the first tubular structure relative to the handle causes advancement of the stent relative to the handle toward the distal end of the delivery system.

The present inventive methods, devices, and stent delivery systems are particularly useful for use with self-expanding stents, including polymeric self-expanding stents, such as the Polyflex stent, which includes polyethylene terephthalate (PET) filaments having a silicone covering. In particular, because such polymeric self-expanding stents will set if they are premounted on a delivery device well in advance of implantation, such stents need to be loaded onto a delivery device by a physician just prior to implantation. The present inventive methods, devices, and stent delivery systems allow for such loading immediately prior to implantation.

These and other features of the invention will be better understood through a study of the following detailed description and accompanying drawings.

BRIEF DESCRIPTION OF THE DRAWINGS

FIG. 5 is a perspective view of an inner tubular structure having a tip preassembled thereon being inserted into an outer tubular structure having a stent partially loaded therein in accordance with a method of the present invention.

FIG. 6 is a perspective view of the outer tubular structure of FIG. 5 having the inner tubular structure shown in FIG. 5 partially inserted therein in accordance with a method of the present invention.

FIG. 7 is a perspective view of the outer tubular structure of FIG. 6 having the inner tubular structure shown in FIG. 5 fully inserted therein to form a stent delivery device in accordance with a method of the present invention.

FIGS. 35a-35c are cross-sectional views illustrating how a tip and inner tubular member of the subject invention may be attached by means of a key and slot.

FIGS. 36a-36c are cross-sectional views illustrating how a tip and inner tubular member of the subject invention may be attached by means of barbs.

FIGS. 38a-38c and 39a-39c are cross-sectional views illustrating how a tip and inner tubular member of the subject invention may be attached by means of hooks and loops.

DETAILED DESCRIPTION OF THE INVENTION

This subject invention pertains to assembly devices for deploying a stent, or other device as described herein, in a bodily passageway. Deployment may be achieved for medical applications (particularly, endoscopic therapy) in the gastrointestinal tract, the biliary tract, the urinary tract, and the respiratory tract. Moreover, the assembly devices may be deployed in the neurological system (e.g., in the brain) and in the cardiovascular system (e.g., in the heart, veins, and arteries). Reference to bodily passageways may be to passageways in any of the aforementioned tracts and systems or elsewhere in the body. The assembly devices are particularly useful during endoscopy procedures in the gastrointestinal tract and biliary tract. For instance, the assembly devices are particularly useful for deployment in the esophagus during endoscopy procedures.

It should be noted that references herein to the term "distal" are to a direction away from an operator of the subject invention, while references to the term "proximal" are to a direction towards the operator of the subject invention. Accordingly, when the terms "distal" and "proximal" are used herein in the context of an assembly device that is being deployed by an operator within a body, such as a human body, the term "distal" refers to a location within the body that is further within the body than a location that is "proximal" to the operator.

Figure 1:
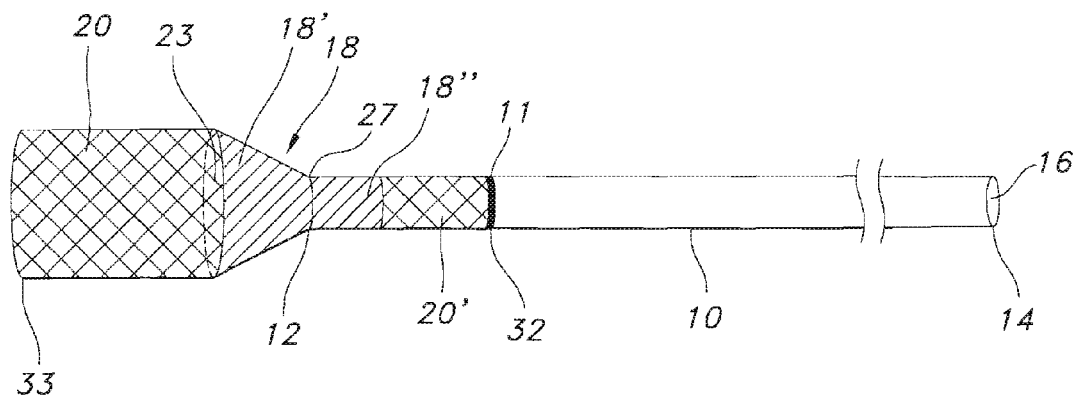
FIG. 1 is a perspective view of a tubular structure having a stent partially constrained therein in accordance with the subject invention.

With reference to the drawings, FIG. 1 shows a perspective view of a tubular structure for use as an exterior tubular structure 10 in the assembly device of the subject invention. As shown in FIG. 1, the exterior tubular structure 10 has a proximal end 12, a distal end 14, and a lumen 16 that extends along the length of the exterior tubular structure 10. The exterior tubular structure 10 may have any suitable length and diameter. Desirably, the exterior tubular structure 10 may have a uniform or substantially uniform diameter throughout its entire length.

As shown in FIG. 1, the exterior tubular structure 10 may have a marker 11 thereon. The marker 11 serves to indicate the distal position of a stent 20 as it is inserted into the exterior tubular structure 10 during assembly of the deployment device of the subject invention.

The marker 11 may be made from any suitable marker material known in the art. Suitable marker materials include any marker material which is normally visible, such as ink and thread. Suitable marker materials also include any radiopaque material such as, for example, tantalum and barium sulfate. Desirably, the exterior tubular structure 10 may be made from a transparent extrusion material such that the stent 20 may be visible within the exterior tubular structure 10 upon insertion of the stent 20 therein. For purposes of illustration, the exterior tubular structure 10 is shown as a transparent extrusion material in FIGS. 1-3, 5-7, 12-13 and 24-25.

In some embodiments, an exterior tubular structure 10 may have a handle 18 positioned on its proximal end 12, as further shown, for example, in FIG. 1. Desirably, the handle 18 may be designed to facilitate easy and gradual loading and constrainment of a stent 20 within the exterior tubular structure 10. In some embodiments, the handle 18 may have a funneled or conical section 18' and a straight portion 18". For instance, the handle 18 depicted in FIG. 1 is funnel-shaped. With reference to FIG. 1, it will be understood that handle 18 is positioned over at least a portion of proximal end 12 of exterior tubular structure 10 such that the proximal end 12 of exterior tubular structure 10 is aligned with the distal end 27 of funneled or conical section 18' of handle 18.

Figure 21:
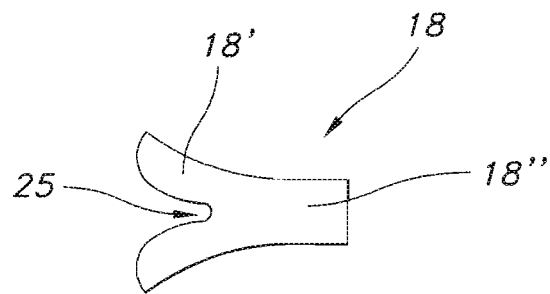
FIG. 21 is a lengthwise cross-sectional view of a handle for use with the present invention having a funneled or conical section which has a rounded interior.

Desirably, funneled or conical section 18' of handle 18 is designed to facilitate loading of stent 20 therein. For example, in some embodiments, funneled or conical section 18' may be split to facilitate loading of a stent 20 and then reassembled upon loading. Moreover, in some embodiments, funneled or conical section 18' may have a flat conical interior 23, as shown in FIG. 1. In other embodiments, funneled or conical section 18' of handle 18 may have a rounded interior 25, as shown in FIG. 21.

In some embodiments of the subject invention, a portion of a stent 20 may be first inserted through the handle 18 of the exterior tubular structure 10 and into the lumen 16 of the exterior tubular structure 10 as shown in FIG. 1. The diameter of the portion of the stent 20 may change to conform to the diameter of the handle 18 and to the diameter of the exterior tubular structure 10 upon passage into the exterior tubular structure 10. By using a handle 18 having a funneled or conical section 18', it may be possible to allow the diameter of the stent 20 to decrease gradually upon insertion through the handle 18 and into the exterior tubular structure 10.

In some embodiments, the stent 20 may be only partially inserted into the tubular structure 10 as shown in FIG. 1. Desirably, in some embodiments, the stent 20 may be partially inserted such that the distal end 32 of the stent 20 may be aligned with the marker 11 of exterior tubular structure 10, as shown in FIG. 1. As further shown in FIG. 1, the portion of the stent 20 that may be inserted into the tubular structure 10 may be in a constrained state relative to the portion of the stent 20 that is not inserted into the tubular structure 10 and relative to the portion of the stent 20 that may be passed through the handle 18. As used herein, the term "partially constrained stent" refers to a stent 20 that may be partially inserted into an exterior tubular structure 10 as shown in FIG. 1 such that at least a portion of the stent may be in a constrained state.

Figure 24:
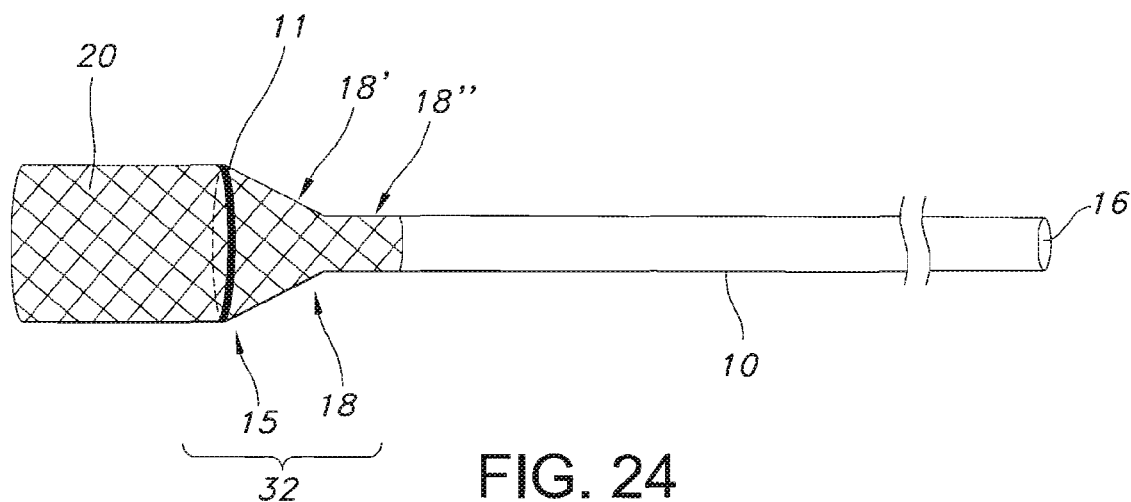
FIGS. 24-25 are perspective views of tubular structures having a stent with a marker partially constrained therein in accordance with a method of the subject invention.
Figure 25:
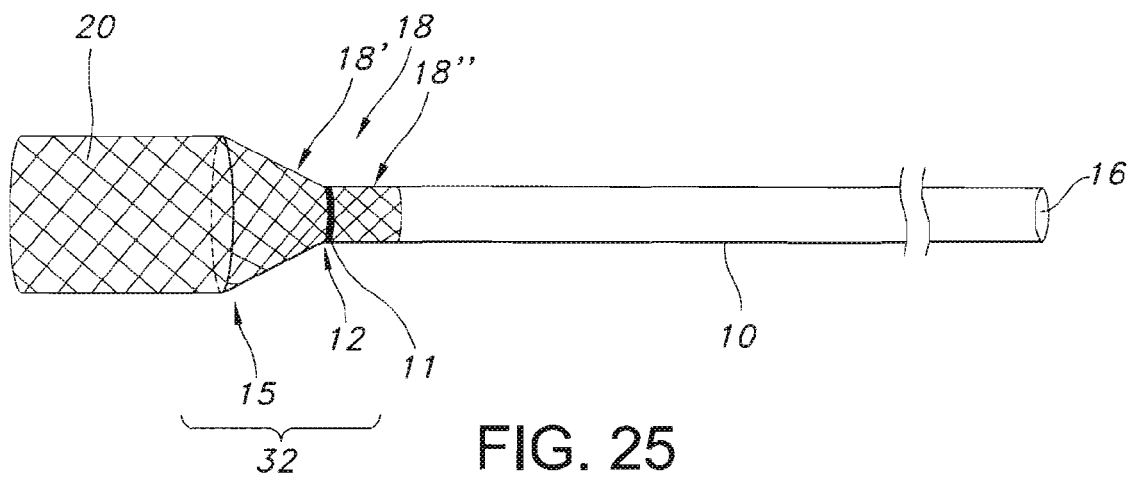

In some embodiments, stent 20 may have a marker 11 thereon. In particular, when exterior tubular structure 10 and handle 18 are translucent or opaque as shown in FIGS. 24 and 25, stent 20 may have a marker 11 thereon. Desirably, marker 11 is positioned on distal end 32 of stent 20. In some embodiments, stent 20 is partially inserted into an exterior tubular structure 10 having base portion 18" of handle 18 thereon until marker 11 on stent 20 is aligned with the proximal end 15 of the funneled or conical section 18' of handle 18, as shown in FIG. 24, or with the proximal end 12 of exterior tubular structure 10, as shown in FIG. 25.

In some embodiments, stent 20 may have a means 19 for compressing the stent 20 thereon to facilitate loading of the stent 20 into the exterior tubular structure 10 and, more particularly, into the handle 18 which may be positioned on exterior tubular structure 10. Desirably, means 19 can be used alone or in conjunction with manual manipulation to facilitate loading of the stent 20.

Figure 22:
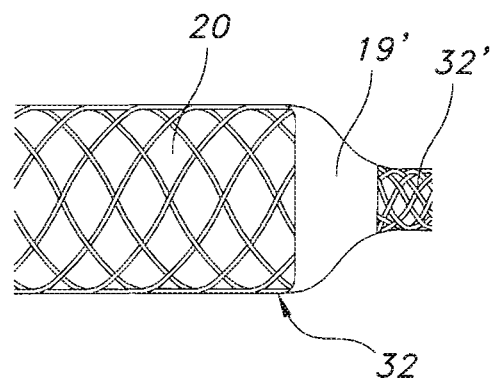
FIG. 22 is a longitudinal view of a stent which has a distal end which is compressed by a structure or device.

In some embodiments, means 19 for compressing the stent 20 is a structure or device 19' which is capable of compressing the distal end 32 of the stent 20, as shown in FIG. 22, which depicts a stent 20 for use in accordance with the present invention having a distal end 32' which is compressed by such a structure or device 19'. In particular, in such embodiments, structure or device 19' may be, for example, a funnel introducer, as shown in FIG. 22. By "funnel introducer" is meant a means or device (besides manual manipulations) that may slightly compress the distal end 32 of the stent 20 to conform the stent 20 to the conical or funneled section 18' of handle 18 and thereby facilitate entry of the stent 20 through handle 18 and into exterior tubular structure 10. As shown in FIG. 22, distal end 32 of a stent 20 assumes a compressed state 32' as a result of the use of structure or device 19'.

Figure 23:
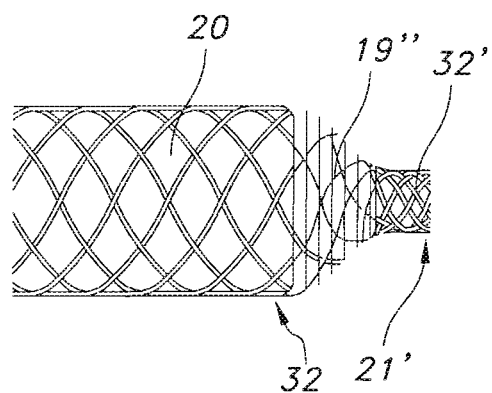
FIG. 23 is a longitudinal view of a stent which has a distal end which is compressed by means of a packaging material.

In other embodiments, the means 19 for compressing the stent 20 may be any suitable packaging material 19", as shown in FIG. 23, which is a perspective view of a stent 20 for use in accordance with the present invention having a distal end 32 which is compressed by such a packaging material 19". In still other embodiments, no means 19 for compressing the stent 20 is applied. In such embodiments, manual manipulation may be employed to compress the distal end 32 of stent 20 to facilitate entry of the stent 20 into the exterior tubular structure 10 and, more particularly, into handle 18, when stent 20 is inserted therein as shown in FIG. 1. As shown in FIG. 23, distal end 32 of stent 20 assumes a compressed state 32' as a result of the use of the packaging material 19".

Figure 2:
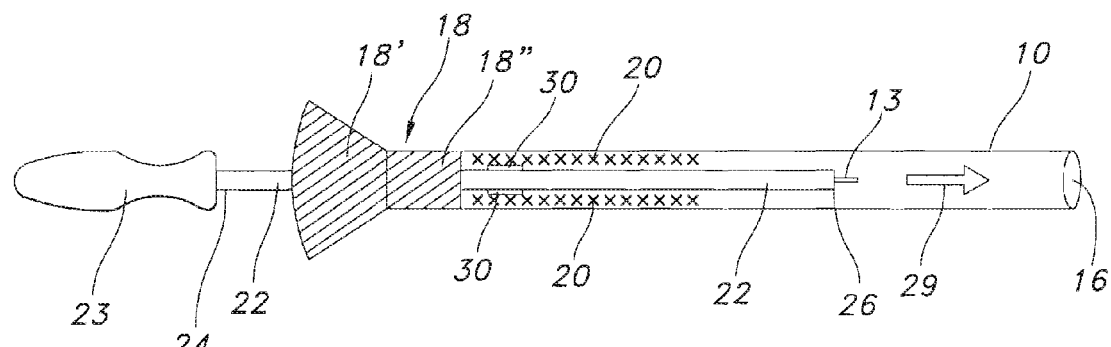
FIG. 2 is a perspective view of the tubular structure of FIG. 1 upon partial insertion of another tubular structure therein in accordance with the present invention.

In some embodiments of the subject invention, the exterior tubular structure 10 may be positioned over an inner tubular structure or sheath 22 to constrain the stent 20 between the exterior tubular structure 10 and the inner tubular structure 22 as shown in FIG. 2, which is a perspective view of an exterior tubular structure 10 and inner tubular structure 22 that are so positioned. The exterior tubular structure 10 may be positioned over the inner tubular structure 22 by pushing the exterior tubular structure 10 over the inner tubular structure 22. More particularly, in some embodiments, the inner tubular structure 22 may be "backloaded" into the exterior tubular structure 10 by pushing the distal end 26 of the inner tubular structure 22 through the handle 18 and into an exterior tubular structure 10 having a stent 20 partially constrained therein as described above with regard to FIG. 1. A handle 23 may be positioned on the proximal end 24 of the inner tubular structure 22 to facilitate loading of the inner tubular structure 22 into the exterior tubular structure 10, as shown in FIG. 2. As further shown in FIG. 2, the exterior tubular structure 10 has a lumen 16 extending therethrough.

The inner tubular structure 22 may be the "backbone" of the delivery assembly devices and systems provided herein. Desirably, the inner tubular structure 22 provides column strength, pushability, and trackability when a delivery system of the subject invention is pushed into an opening/tract of the human body (such as the esophagus, an airway, a vessel or other body conduit). In general, the inner tubular structure 22 may be made from an extrusion material. Non-limiting examples of extrudable materials which could be useful for outer 10 and inner 22 tubular structures include any plastic or polymeric material. Desirably, the material is somewhat hard but is a flexible plastic or polymeric material.

The exterior tubular structure 10 may be transparent or translucent, and is, desirably, substantially or partially transparent or translucent. Furthermore, the tubular structure 10 may be constructed of any suitable biocompatible materials, such as, but not limited to, polymers and polymeric materials, including fillers such as metals, carbon fibers, glass fibers or ceramics. Other useful materials for exterior tubular structure 10 include, but are not limited to, polyethylene, polypropylene, polyvinyl chloride, polytetrafluoroethylene, fluorinated ethylene propylene, polystyrene, poly(ethylene terephthalate), polyurethane, silicone rubbers, polyamides, polyimides, polycarbonates, and polyether ether ketone. The exterior tubular structure may also include a braided structure to improve mechanical properties such as tensile, column strength and/or kink resistance. Desirably, exterior tubular structure 10 is formed from polytetrafluoroethylene (PTFE).

The inner tubular structure 22 may be constructed of any suitable biocompatible materials, such as, but not limited to, polymers and polymeric materials, including fillers such as metals, carbon fibers, glass fibers or ceramics. Other useful materials for inner tubular structure 22 include, but are not limited to, polyethylene, polypropylene, polyvinyl chloride, fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof.

The inner tubular structure 22 may have any suitable length and diameter, as long as the diameter of the inner tubular structure 22 is less than the diameter of the exterior tubular structure 10.

In some embodiments of the subject invention, a means 30 for moving stent 20 is employed to cause movement of stent 20 within the exterior tubular structure 10 upon insertion of the inner tubular structure 22 therein, as shown in FIG. 2, which shows a stent 20 which has partially been moved within exterior tubular structure 10 as a result of the employment of a means 30 for moving stent 20. In particular, means 30 for moving stent 20 causes movement of the stent 20 within the exterior tubular structure 10 upon insertion of the inner tubular structure 22 therein.

In some embodiments, the means 30 for moving stent 20 moves stent 20 by engaging stent 20 such as by becoming coupled to stent 20. In other embodiments, means 30 for moving stent 20 moves stent 20 by pushing the stent 20 into the desired position.

In some embodiments, a guide wire 13 may be positioned within the inner tubular structure 22 as shown in FIG. 2.

Desirably, means 30 for moving stent 20 causes the stent 20 and the inner tubular structure 22 to move concomitantly within the exterior tubular structure 10. In particular, in some embodiments, when the means 30 for moving stent 20 comes into contact with the stent 20 shown in FIG. 1, the means 30 desirably anchors the stent 20 to the inner tubular structure 22, i.e., locks the stent 20 into position on the inner tubular structure 22, such that distal movement of the inner tubular structure 22 causes the stent 20 to slide distally within the exterior tubular structure 10 in the direction of the arrow 29 shown in FIG. 2.

Figure 26:
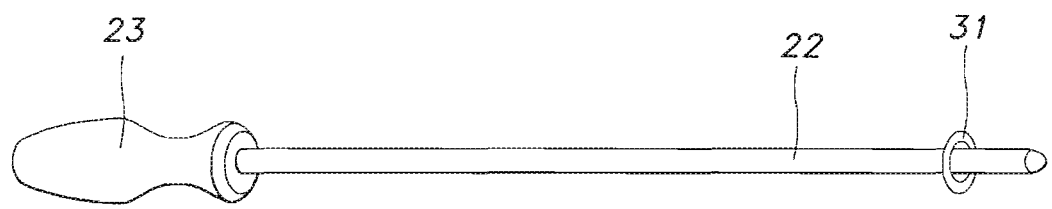
FIG. 26 is a perspective view of an inner tubular structure having an annular protruberance such as an o-ring thereon.

In some embodiments, the means 30 for moving stent 20 may be a stent-engaging member that is a separate and distinct structure from inner tubular structure 22. When such a stent-engaging member is used, the stent-engaging member may be capable of being dis-engagingly attached to inner tubular structure 22. For example, the stent-engaging member may be an annular protuberance 31 such as an o-ring that is capable of being slipped onto the inner tubular structure 22, as shown in the perspective view of FIG. 26. Such a stent-engaging member may be attached to the inner tubular structure 22 by any suitable method known in the art. For example, the stent-engaging member may be molded onto the inner tubular structure 22.

Figure 27:
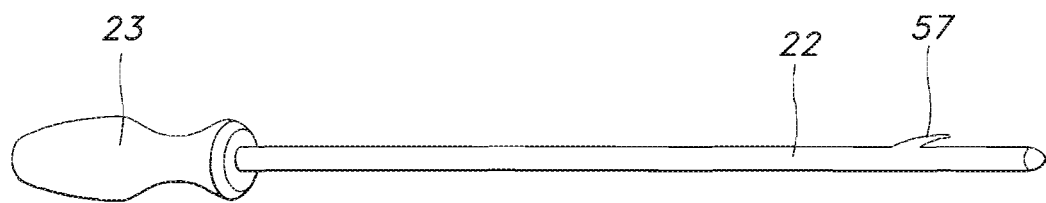
FIG. 27 is a perspective view of an inner tubular structure having a flap thereon.
Figure 28:
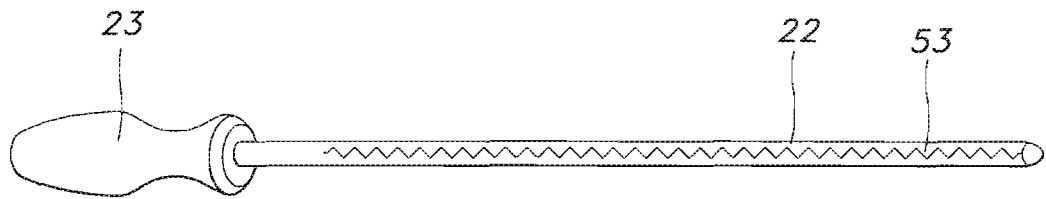
FIG. 28 is a perspective view of an inner tubular structure having a pattern thereon.
Figure 29:
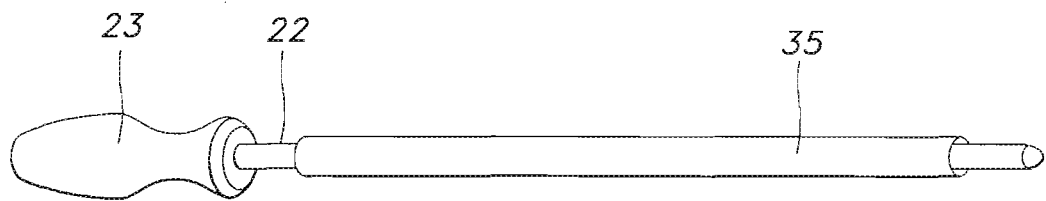
FIG. 29 is a perspective view of an inner tubular structure having a compressive and/or a tacky/sticky layer thereon.
Figure 30:
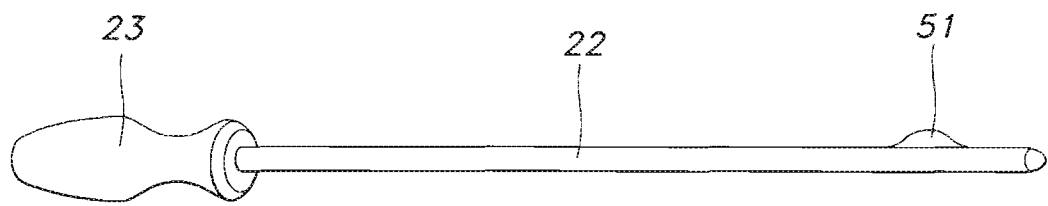
FIG. 30 is a perspective view of an inner tubular structure having a bump thereon.
Figure 31:
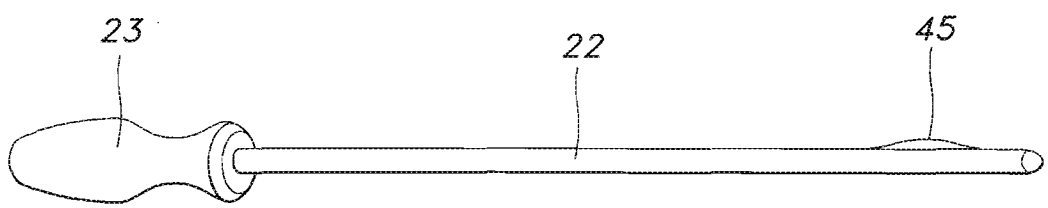
FIG. 31 is a perspective view of an inner tubular structure having an annular ridge thereon.
Figure 32:
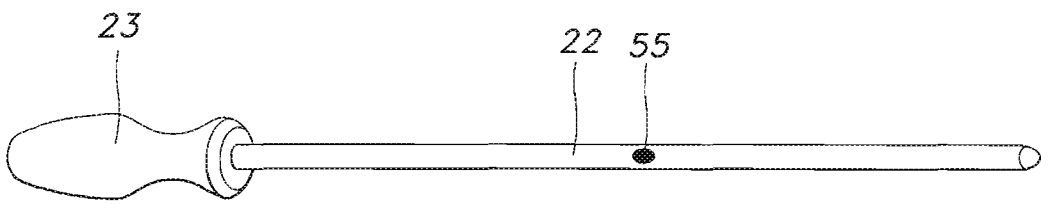
FIG. 32 is a perspective view of an inner tubular structure having a divot therein.

In other embodiments, the means 30 for moving stent 20 is a stent-engaging portion that is part of the inner tubular structure 22 itself. When the means 30 for engaging stent 20 is a part of the inner tubular structure 22, the means 30 may be, for example, a flap 57 which is cut into inner tubular structure 22, as shown in FIG. 27. In other embodiments, when the means 30 for moving stent 20 is a part of the inner tubular structure 22, the means 30 may be a pattern 53 or at least one divot 55 in structure 22, as shown in FIGS. 28 and 32, respectively. In yet other embodiments, when the means 30 for moving stent 20 is a part of the inner tubular structure 22, the means 30 may be a compressive and/or a tacky/sticky layer 35, as shown in FIG. 29. Although layer 35 is shown on only a portion of inner tubular structure 22 in FIG. 29, it will be understood that layer 35 may span the entire length of inner tubular structure 22. In still other embodiments, when the means 30 for moving stent 20 is a part of the inner tubular structure 22, the means 30 may be a bump 51, as shown in FIG. 30, or an annular ridge 45, as shown in FIG. 31. Although not shown, it will be understood that inner tubular structure may have more than one of any of the aforementioned means 30 for moving stent 20 thereon and any combination thereof.

In some embodiments, when it is desired to re-constrain the stent 20 after partial deployment within the exterior tubular structure 10, it may be especially useful to hold the stent 20 in position on the inner tubular structure 22 by means of the dis-engagable means 30 for moving the stent 20 for the purpose of moving the stent 20 into the loaded position such that the delivery system may be subsequently delivered into the body lumen and the stent 20 deployed thereafter. In such embodiments, the exterior tubular structure 10 may be pushed back over the stent 20 without the stent 20 sliding along with the exterior tubular structure 10.

Figure 3:
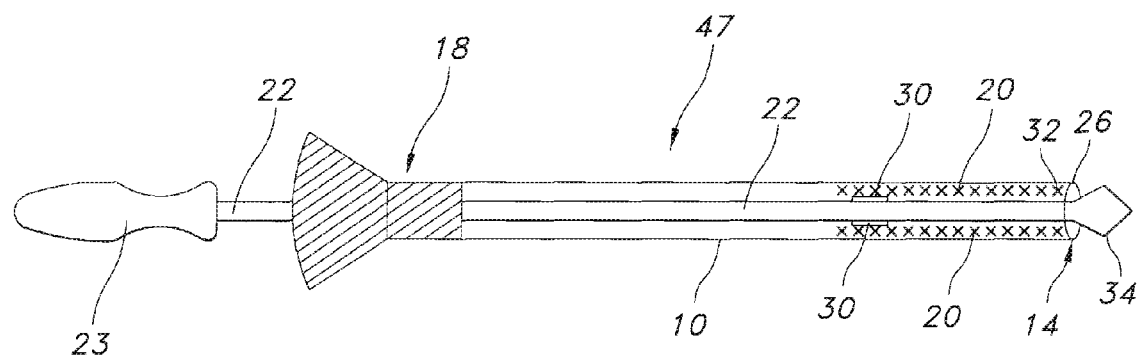
FIG. 3 is a perspective view of a tubular structure upon complete insertion of another tubular structure therein to form a fully-loaded stent assembly device in accordance with the present invention.

FIG. 3 shows a stent delivery device 47 of the present invention in its final form before use. As shown in the perspective view of FIG. 3, the distal end 26 of the inner tubular structure 22 may be aligned with the distal end 14 of the exterior tubular structure 10. When the distal end 26 of the inner tubular structure 22 is aligned with the distal end 14 of the exterior tubular structure 10, the distal end 32 of the stent 20 also is desirably aligned with the distal end 14 of the exterior tubular structure 10, as further shown in FIG. 3. In such embodiments, the stent 20 may be fully constrained within the exterior tubular structure 10, i.e., the stent 20 may be fully covered by the exterior tubular structure 10 such that it is in a constrained state relative to its free state.

As shown in FIG. 3, the delivery system of the present invention may include a tip 34 which is attached to the distal end 26 of the inner tubular structure 22 as shown in FIG. 3. Tip 34 desirably imparts a "softer," more flexible profile to the delivery system, thus improving the assembly device profile when the assembly device is pushed and tracked through tortuous, narrow, luminal anatomy.

Tip 34 shown in FIG. 3 may be assembled onto the distal end 26 of the inner tubular structure 22 either prior to the insertion of the inner tubular structure 22 into the exterior tubular structure 10 or after the insertion of the inner tubular structure 22 into the exterior tubular structure 10.

In embodiments where the tip 34 is preassembled on the inner tubular structure 22, tip 34 may be compressible and desirably capable of expansion. In particular, when tip 34 is preassembled on inner tubular structure 22, tip 34 may assume a reduced profile 34' when the inner tubular structure 22 having tip 34 attached thereto is passed through a partially loaded stent 20 prior to the means 30 for moving stent 20 engaging the stent 20, as shown in the perspective view in FIG. 5. Desirably, the tip 34 may be designed to minimize the amount of friction that occurs between the stent 20 and the tip 34 upon insertion of the inner tubular structure 22 within the stent 20.

Tip 34 then may assume an expanded profile 34" after the means 30 for moving stent 20 engages the stent 20, as shown in the perspective view in FIG. 6. In some embodiments, at least a portion of a tip 34" having an expanded profile may come into contact with at least a portion of the exterior tubular structure 10 during passage therein as shown in FIG. 6. In yet other embodiments, when the tip 34 is preassembled onto the inner tubular structure 22, the tip 34 may maintain a reduced profile 34' until the tip 34 is pushed outside of the exterior tubular structure 10, at which point the tip assumes an expanded profile 34" as shown in the perspective view in FIG. 7, which shows a stent delivery device 49 of the present invention which is ready for deployment in a bodily lumen. In such embodiments, the exterior tubular structure 10 constrains the tip 34 while the same is being "back-loaded" into the exterior tubular structure 10.

As noted above, in some embodiments, tip 34 may be assembled onto inner tubular structure 22 after insertion of the inner tubular structure 22 into the exterior tubular structure 10. In such embodiments, the inner tubular structure 22 is inserted into exterior tubular structure 10 such that the distal end 26 of the inner tubular structure 22 is aligned with the distal end 14 of the exterior tubular structure 10. Thereafter, tip 34 is attached to the inner tubular structure 22 to form the stent delivery system 47 of the present invention as shown in FIG. 3.

The tip 34 may have any suitable design and may be attached to the inner tubular structure 22 using any suitable method. For example, tip 34 and inner tubular structure 22, as shown in FIGS. 5-7, may be attached together by means of, for example, a snap-fit, clip or screw-on assembly method and any other suitable attachment means known in the art.

Figure 8A:
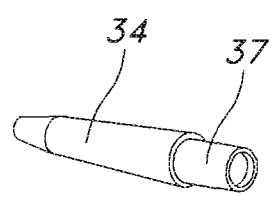
FIGS. 8a-8e are perspective views illustrating how a tip and inner tubular member of the subject invention may be attached by means of a push-lock.
Figure 8B:
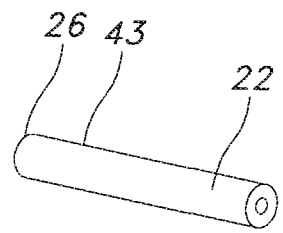
Figure 8C:
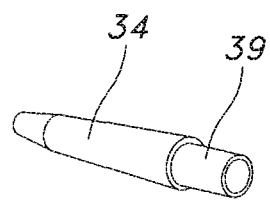
Figure 8D:
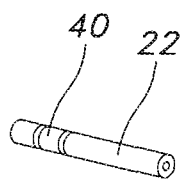
Figure 8E:
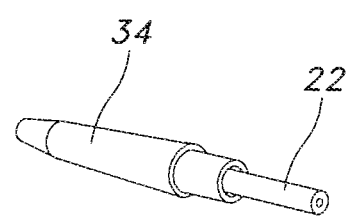

Another method of attaching tip 34 to inner tubular structure 22 involves a "push-on lock" that interacts with the distal end 26 of the inner tubular structure 22, as shown in FIGS. 8a-8e. In particular, as shown in the perspective view in FIG. 8a, the tip 34 may have a portion 37 that interlocks with a portion 43 of an inner tubular structure 22 upon insertion therein, as shown in the perspective view in FIG. 8b. Alternatively, the tip 34 may have a portion 39 as shown in the perspective view in FIG. 8c into which an inner tubular structure 22 can be inserted. An inner tubular structure 22 suitable for insertion into such a tip 34 is shown in FIG. 8d and may have a portion 40 that interlocks with the portion 39 of the tip 34 shown in FIG. 8c to lock the tip 34 and inner tubular structure 22 together as shown in FIG. 8e. A tip 34 as shown in FIG. 8a may desirably be attached to an inner tubular structure 22 as shown in FIG. 8b as a final step in the assembly of the stent-delivery systems disclosed herein.

Figure 9:
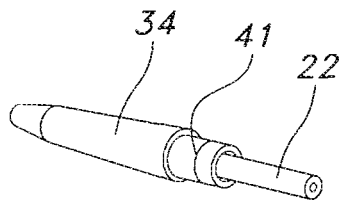
FIG. 9 is a perspective view illustrating how a tip and inner tubular member of the subject invention may be attached by means of a thread.

In some embodiments, a tip 34 as shown in FIG. 8a may be threaded to the distal end 26 of the inner tubular structure 22 shown in FIG. 8b. A tip 34 and an inner tubular structure 22 attached by means of a thread 41 is shown in the perspective view in FIG. 9. Affixing a tip 34 to an inner tubular structure 22 in such a manner may desirably be the final step in the assembly of the stent-delivery systems disclosed herein.

Figure 10A:
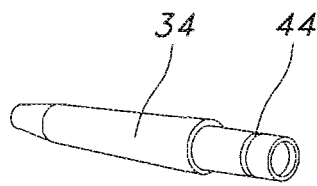
FIGS. 10a-10c are perspective views illustrating how a tip and inner tubular member of the subject invention may be attached by means of a clip.
Figure 10B:
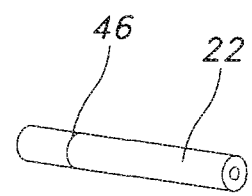
Figure 10C:
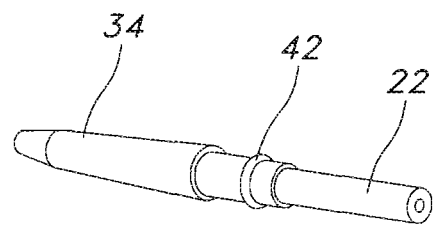

Another method for attaching a tip 34 to an inner tubular structure 22 involves a clip-retaining method. In this method, an inner tubular structure 22 having a slot 46 therein, as shown in the perspective view in FIG. 10b, is inserted into a tip 34 having a slot 44 therein, as shown in the perspective view in FIG. 10a. Upon insertion of the inner tubular structure 22 into the tip 34, the slot 46 of the inner tubular structure 22 aligns with the slot 44 of the tip 34. A locking clip 42 may then be placed into the slot 46 of the inner tubular structure and the slot 44 of the tip 34 to affix the tip 34 to the inner tubular structure 22 as shown in the perspective view in FIG. 10c. A tip 34, as shown in FIG. 10a, may desirably be attached to an inner tubular structure 22, as shown in FIG. 10b, as a final step in the assembly of the stent-delivery systems disclosed herein.

Figure 11A:
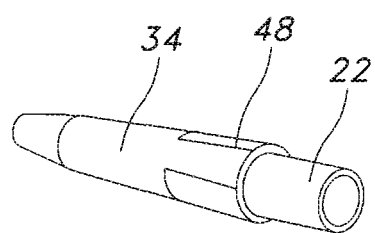
FIGS. 11a-11c are perspective views illustrating how a tip having collapsible hinges or fins may be inserted into an exterior tubular structure of the subject invention.
Figure 11B:
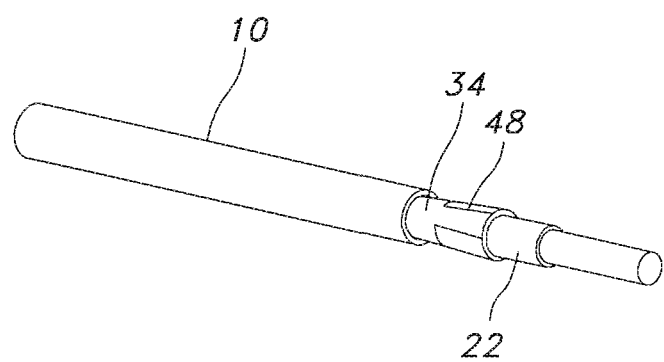
Figure 11C:
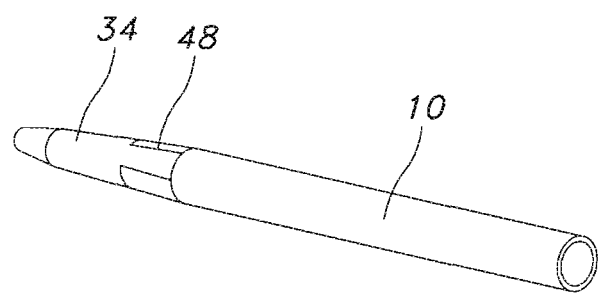

In yet another method, an inner tubular structure 22 may be inserted into a tip 34 having collapsible hinges or fins 48, as shown in the perspective view in FIG. 11a. Desirably, the collapsible hinges or fins 48 flex to allow the tip 34 to be loaded into an exterior tubular structure 10 of the subject invention as shown in the perspective view in FIG. 11b using the method described above with regard to FIGS. 1 and 2. After the tip 34 emerges from the exterior tubular structure 10, the collapsible hinges or fins 48 may desirably open up to prevent the tip 34 from being retracted into the exterior tubular structure 10, as shown in the perspective view in FIG. 11c.

In some embodiments, tip 34 may be attached to inner tubular structure 22 by means of an adhesive. Additionally, or in the alternative, the tip 34 may be molded over the inner tubular structure 22. Desirably, the tip 34 and inner tubular structure 22 shown in FIGS. 11a-11c may be attached by either or both of these methods.

Figure 4A:
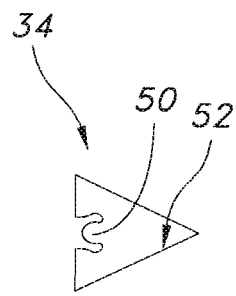
FIGS. 4a-4c are cross-sectional views illustrating how a tip and inner tubular member of the present invention may be attached by means of a bump on the inner surface of tip.
Figure 4B:
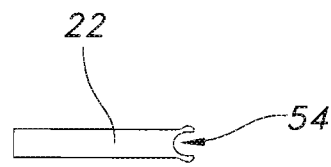
Figure 4C:
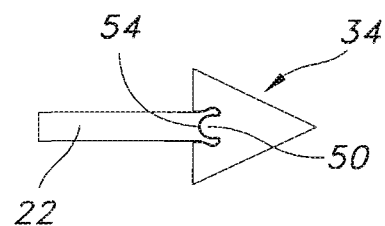

In still other embodiments, tip 34 may be attached to inner tubular structure 22 by means of one or more structures which are inherent to tip 34. In particular, tip 34 may include a clip or lock 50 on the inner surface 52 of tip 34, as shown in the cross-sectional view of tip 34 shown in FIG. 4a. In such embodiments, inner tubular structure 22 may include a groove or indentation 54, as shown in FIG. 4b, which is capable of engaging clip or lock 50 to attach inner tubular structure 22 to clip or lock 50, as shown in FIG. 4c. Although not shown, it will be understood that tip 34 may include a groove or indentation 54 on its inner surface 52 and inner tubular structure 22 may include a clip or lock 50 which is capable of engaging the groove or indentation 54 on the inner surface 52 of tip 34 to attach tip 34 to inner tubular structure 22.

In other embodiments, tip 34 may include a bump or hole on its inner surface 52, and inner tubular structure 22 may contain the other of said bump or hole. Bump or hole on said inner tubular structure 22 may then engage with the other of said bump or hole which is on the inside surface of tip 34 to "click" inner tubular structure 22 into place in the inside of tip 34.

Figure 33A:
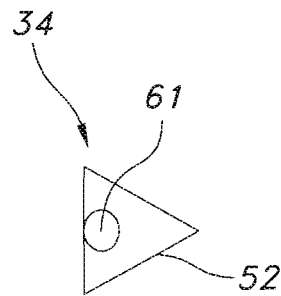
FIGS. 33a-33c and 34a-34c are cross-sectional views illustrating how a tip and inner tubular member of the subject invention may be attached by means bumps and holes.
Figure 33B:
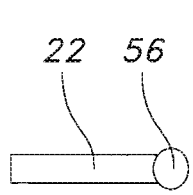
Figure 33C:
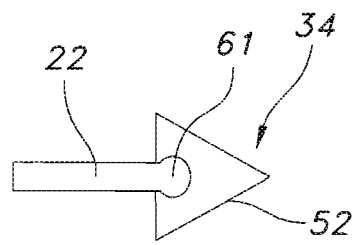

With reference to FIG. 33a, which is a cross-sectional view of a tip 34, that figure illustrates tip 34 having a hole 61 on its inner surface 52. In such embodiments, inner tubular structure 22 may include a bump 56, as shown in FIG. 33b, which is capable of engaging hole 61 of tip 34, as shown in FIG. 33c to attach tip 34 to inner tubular structure 22.

Figure 34A:
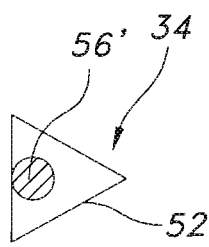
Figure 34B:
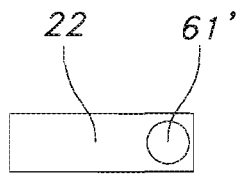
Figure 34C:
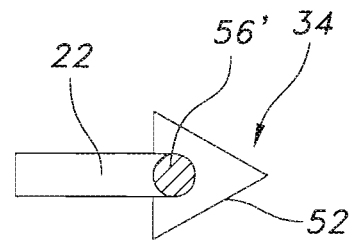

With reference to FIG. 34a, which is a cross-sectional view of a tip 34, that figure illustrates tip 34 having a bump 56' on its inner surface 52. In such embodiments, inner tubular structure 22 may include a hole 61', as shown in FIG. 34b, which is capable of engaging bump 56' to attach tip 34 to inner tubular structure 22, as shown in FIG. 34c.

In yet other embodiments the inside of tip 34 may include a key or slot and the inner tubular structure 22 may include the other of said key or slot. With reference to FIG. 35a, which is a cross-sectional view of a tip 34, that figure illustrates tip 34 having a slot 58 within the inner surface 52 of tip 34. In such embodiments, inner tubular structure 22 may include a key 60, as shown in FIG. 35b, which is capable of engaging slot 58 to attach tip 34 to inner tubular structure 22, as shown in FIG. 35c. Although not shown, it will be understood that tip 34 may include a key 60 on its inner surface 52 and inner tubular structure 22 may include a slot 58 which is capable of engaging the key 60 on the inner surface 52 of tip 34 to attach tip 34 to inner tubular structure 22.

In yet other embodiments, inner tubular structure 22 may be attached to tip 34 by means of barbs. With reference to FIG. 36a, which is a cross-sectional view of a tip 34, that figure illustrates tip 34 having barbs 62 on the inner surface 52 of tip 34. In such embodiments, inner tubular structure 22 also may include barbs 62', as shown in FIG. 36b, which are capable of engaging barbs 62 on inner surface 52 of tip 34 to attach tip 34 to inner tubular structure 22 as shown in FIG. 36c.

Figure 37A:
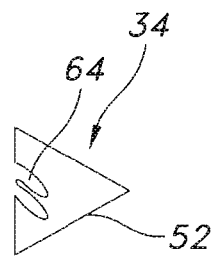
FIGS. 37a-37c are cross-sectional views illustrating how a tip and inner tubular member of the subject invention may be attached by means of ribs.
Figure 37B:
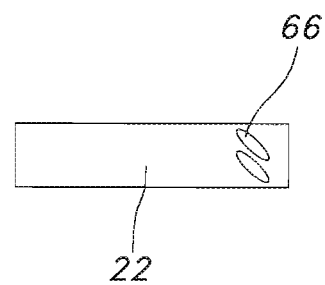
Figure 37C:
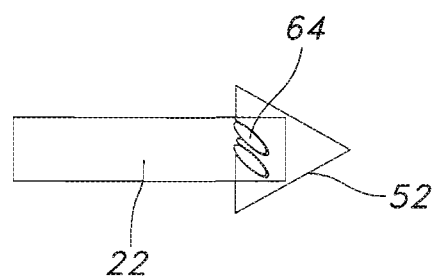

In still other embodiments, inner tubular structure 22 may be attached to tip 34 by means of ribs. With reference to FIG. 37a, which is a cross-sectional view of a tip 34, that figure illustrates tip 34 having ribs 64 on its inner surface 52. In such embodiments, inner tubular structure 22 may include indentations 66, as shown in FIG. 37b, which are capable of engaging ribs 64 on inner surface 52 of tip 34 to attach tip 34 to inner tubular structure 22 as shown in FIG. 37c. Although not shown, tip 34 may include indentations 66 on its inner surface 52 and inner tubular structure 22 may include ribs 64 which are capable of engaging indentations 66 on the inner surface 52 of inner tubular structure 22 to attach tip 34 to inner tubular structure 22.

In yet other embodiments, inner tubular structure 22 may be attached to tip 34 by means of hooks and loops (such as Velcro). In such embodiments, when inner tubular structure 22 includes one of said hooks and loops, tip 34 includes the other of said hooks and loops.

Figures 38A, 38B:
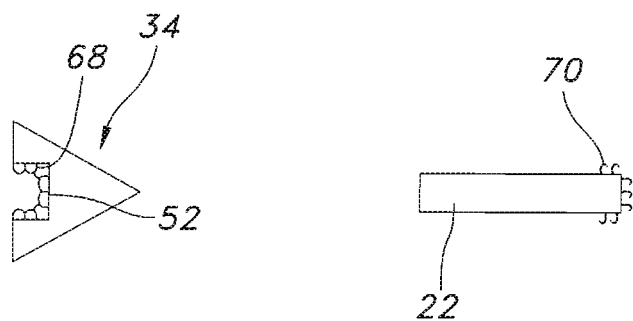
Figure 38C:
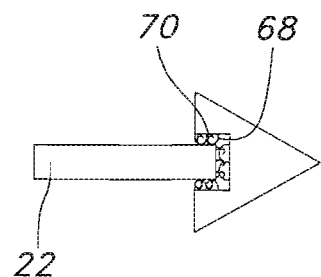

With reference to FIG. 38a, which is a cross-sectional view of a tip 34, that figure illustrates tip 34 having loops 68 on its inner surface 52. In such embodiments, inner tubular structure 22 may include hooks 70, as shown in FIG. 38b, which are capable of engaging loops 68 on inner surface 52 of tip 34 to attach tip 34 to inner tubular structure 22, as shown in FIG. 38c.

With reference to FIG. 39a, which is a cross-sectional view of a tip 34, that figure illustrates tip 34 having hooks 70' on its inner surface 52. In such embodiments, inner tubular structure 22 may include loops 68', as shown in FIG. 39b, which are capable of engaging hooks 70' to attach tip 34 to inner tubular structure 22, as shown in FIG. 39c.

Figure 12:
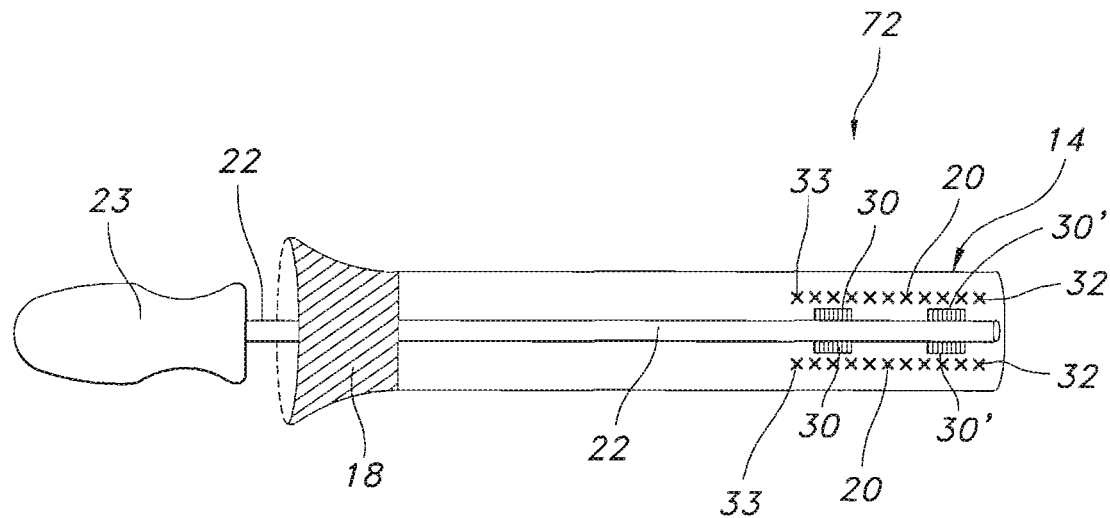
FIG. 12 is a perspective view of an outer tubular structure having an inner tubular structure and stent inserted therein, wherein the stent is engaged to the inner tubular structure by means of two stent-engaging portions.

Desirably, in some embodiments of the subject invention, two or more means 30, 30' for moving a stent 20 may be used in the stent delivery devices. Desirably, one means 30 for moving a stent 20 may be positioned on the inner tubular structure 22 such that it becomes attached to the proximal end 33 of the stent 20 as shown in FIG. 12, which is a perspective view of an exterior tubular structure 10 having an inner tubular structure 22 and stent 20 inserted therein in the manner described above with regard to FIGS. 1 and 2. The other means 30' for moving a stent 20 may be positioned on the inner tubular structure 22 such that it becomes coupled to the distal end 32 of the stent 20, as further shown in FIG. 12. With reference to FIG. 12, it will be understood that inner tubular structure 22 having handle 23 thereon is used to load stent 20 through the handle 18 of outer tubular structure 10 as described above with regard to FIGS. 1 and 2. Means 30, 30' for moving stent 20 then move stent 20 to the distal end 14 of the exterior tubular structure 10 upon insertion of the inner tubular structure 22 within outer tubular structure 10 to form a stent delivery device 72 as shown in FIG. 12 which is ready for deployment in the body.

When two or more means 30, 30' for moving a stent 20 are used, the means 30' that may engage the distal end 32 of the stent 20 desirably allows for early catching and sliding of the constrained stent 20, while the means 30 that engages the proximal end 33 of the stent 20 desirably allows for reconstrainment of the stent 20 after partial deployment of the stent 20. Desirably, the stent 20 may be partially deployed such that the stent 20 may have a length that is up to 95% of the length of the stent 20 in its free, non-constrained state. A stent 20 that may be engaged to an inner tubular structure 22 by means of two or more means for moving stent 30, 30' further decreases the risk of stent slippage.

Figure 13:
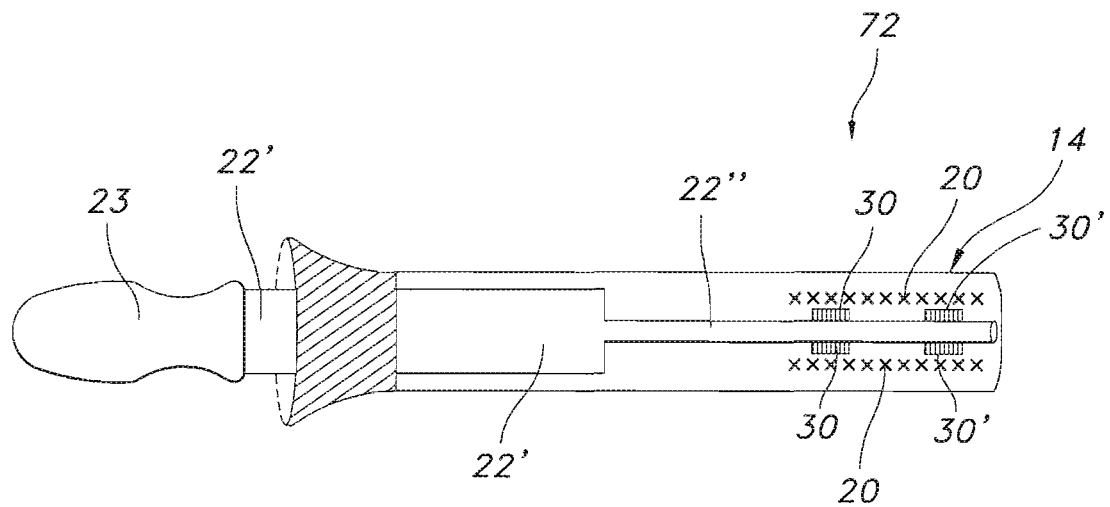
FIG. 13 is a perspective view of an outer tubular structure having an inner tubular structure and stent inserted therein, wherein the inner tubular structure has a non-uniform diameter.

The means 30, 30' for moving stent 20 may be any suitable structures useful for that purpose and may have any suitable design. For example, the means 30 and/or 30' may be a stent holder or anchor component, as shown in FIG. 12. In some embodiments, the means 30 and/or 30' may be a flat holder that increases friction locally between the inner tubular structure 22 and the exterior tubular structure 10, as shown in FIG. 13. In some embodiments, means 30 and/or 30' may be an o-ring. Moreover, or in the alternative, the structure 30 and/or 30' may have fins or teeth or other protrusions thereon to "catch" the stent 20 and hold it in place.

In such embodiments where two or more means 30, 30' for moving stent 20 are used, the structures 30, 30' may be the same or different. In particular, means 30 may have one design while structure 30' has a different design. For example, in some embodiments means 30 may be protrusions, while means 30' may be an o-ring.

In some embodiments of the subject invention, the inner tubular structure 22 may include a proximal portion 22' which is larger than a distal diameter portion 22", as shown in FIG. 13, which is a perspective view of an exterior tubular structure 10 having an inner tubular structure 22 and stent 20 inserted therein in the manner described above with regard to FIGS. 1 and 2. Desirably, the proximal portion 22' will have an outer diameter that is within about 0.1 to 0.5 mm of the inner diameter of the exterior tubular structure 10. Moreover, the diameter of the distal diameter portion 22" of the inner tubular structure 22 is desirably 2-3 mm less than the diameter of the proximal diameter portion 22' of the inner tubular structure 22. Desirably, the distal diameter portion 22" engages the stent to advance the stent forward toward the distal end of the stent delivery system.

The stent 20 of the stent delivery assemblies illustrated herein may be deployed or loaded by pulling on the handle 18 of the exterior tubular structure 10 while maintaining the inner tubular structure 22 in place by grasping the handle 23 of the inner tubular structure. During stent deployment in the body, retracting the exterior tubular structure 10 may allow the stent 20 to release.

Any suitable stent may be used in the stent delivery systems of the present invention. In particular, various stent types and stent constructions may be employed in the invention. Among the various stents useful include, without limitation, self-expanding stents. The stents may be capable of radially contracting as well and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents, including biodegradable and bioabsorbable stents. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like. Examples of various stent configurations are shown in U.S. Pat. No. 4,503,569 to Dotter, U.S. Pat. No. 4,856,561 to Hillstead, U.S. Pat. No. 4,580,568 to Gianturco, U.S. Pat. No. 4,732,152 to Wallsten, and U.S. Pat. No. 5,876,448 to Thompson, all of whose contents are incorporated herein by reference. Braided, knitted, and laser-cut stents are particularly useful.

Figure 40:
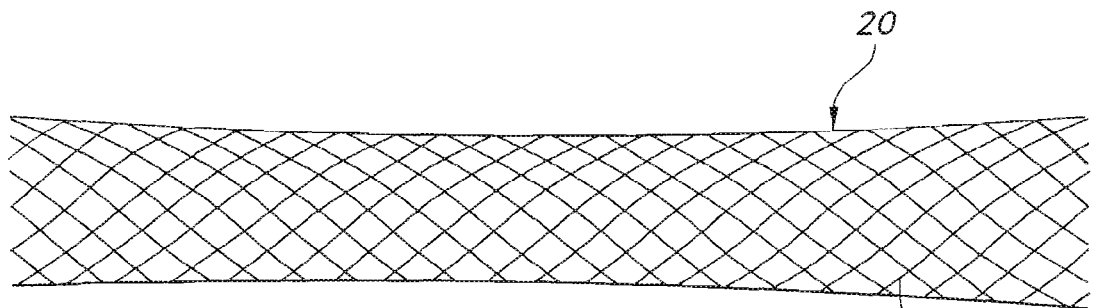
FIG. 40 is an exploded view of a stent for use in the subject invention.

As depicted in FIG. 40, one embodiment of the present invention applies the method and system of the present invention to a braided stent 20. FIG. 40 is an exploded or enlarged view of the stent 20 to depict the braiding of the stent filaments 75. As used herein the term braiding and its variants refer to the diagonal intersection of elongate filaments 75 so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained.

Figure 14:
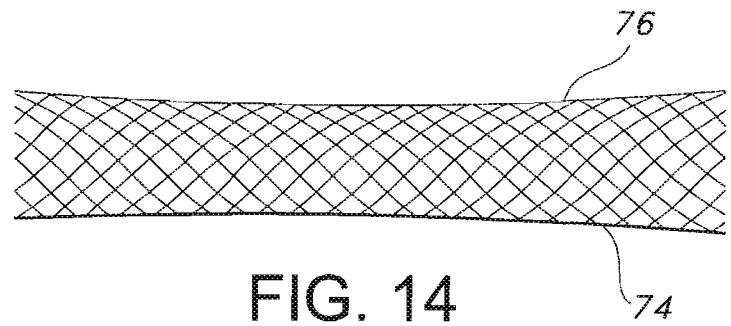
FIG. 14 is a longitudinal view of a wire stent suitable for use in the present invention.

As described above, various stent types and stent constructions may be employed in the invention as the stent 20, and the invention can be constructed to accommodate stents of various sizes and configurations. Non-limiting examples of suitable stent geometries for stent 20 are illustrated in FIGS. 14-20. In particular, stent 20 may be a wire stent 74. As shown in FIG. 14, wire stent 74 is a hollow tubular structure formed from wire strand 76 or multiple wire strands. Wire stent 74 may be formed by, for example, braiding or spinning wire strand(s) 76 over a mandrel (not shown). Wire stent 74 is capable of being radially compressed and longitudinally extended for implantation into a bodily lumen. The degree of elongation depends upon the structure and materials of the wire stent 74 and can be quite varied, for example, about 5% to about 200% of the length of wire stent 74. The diameter of wire stent 74 may also become several times smaller as it elongates.

Unitary stent structures may be obtained by braiding and/or filament winding stent wires to obtain complex stent geometries, including complex stent geometries, including complex bifurcated stents. Alternatively, stent components of different sizes and/or geometries may be mechanically secured by welding or suturing. Additional details of wire stents of complex geometry are described in U.S. Pat. Nos. 6,325,822 and 6,585,758, the contents of which are incorporated herein by reference.

Stent 20 may have one or more atraumatic open end(s). As used herein, the phrase "atraumatic end," and it variants, refers to a terminal end of a stent which is free of sharp wire ends or other sharp projections or deformities which may cause trauma when implanted into a bodily lumen. In particular, the wires of stent 20 may be braided so as to produce an atraumatic end. For example, certain wires of stent 20 may be extended and looped back to provide an atraumatic end having, for example, no sharp or traumatically pointed bends, no sharp wire ends, and no other traumatically sharp projections or deformities or the like.

Figure 15:
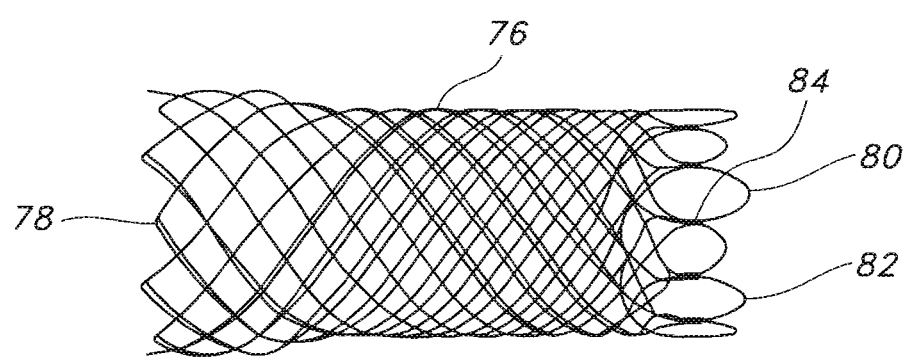
FIG. 15 is a longitudinal view of an atraumatic braided stent for use in the present invention.

In some embodiments, as depicted in FIG. 15, braided stent 76 is desirably an atraumatic stent having no sharp terminating members at one or both of the opposed open ends 78, 80. In particular, such a stent desirably has atraumatic ends, i.e., ends which are free or substantially free of loose wire ends or of other sharp projections. The elongate stent wires terminating at open end 80 are mated to form closed loops 82 and adjacently mated wires are secured to one and the other by mechanical means, such as welds 84. The positioning of adjacently mated wires to form closed-loop end designs is further described in U.S. Patent Application Publication Nos. 2005/0049682 A1 and 2006/0116752 A1, the contents of which are incorporated herein by reference. Desirably, the elongate wires terminating at open end 80 are in a cathedral type arch or loop configuration. Further details of the cathedral type of arch or closed-loop configuration may be found in U.S. Patent Application Publication No. 2005/0256563 A1, the contents of which are incorporated herein by reference. The stent wires at the opposed open end 78 may also be free of any sharp terminating points by, for example, commencing braiding of the wires under tension over a pin (not shown) so that the wire ends terminate just at the end 80, where the wire ends may be looped and welded thereat.

Figure 16:
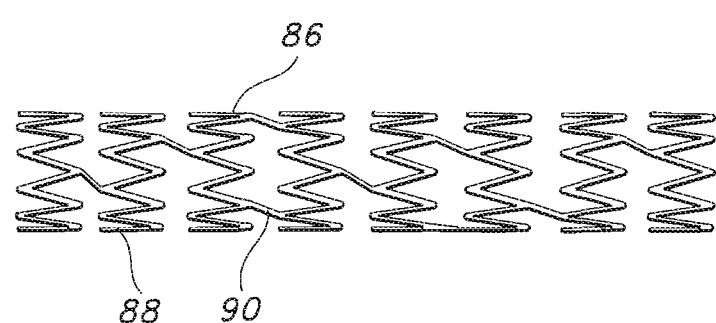
FIG. 16 is a longitudinal view of a zig-zag stent for use in the present invention.
Figure 17:
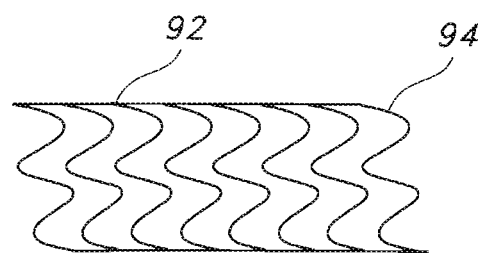
FIG. 17 is a longitudinal view of an alternate zig-zag stent for use in the present invention.

A zig-zag wire stent 86 may also be useful as stent 20. Wire strand 88 may be arranged in what can be described as a multiple of "Z" or "zig-zag" patterns to form a hollow tubular stent. The different zig-zag patterns may optionally be connected by connecting member 90. Further, zig-zag wire stent 86 is not limited to a series of concentric loops as depicted in FIG. 16, but may be suitably formed by helically winding of the "zig-zag" pattern over a mandrel (not shown). For example, as depicted in FIG. 17, zig-zag stent 92 is formed by helically winding at least one stent wire 94 with no interconnections between the helically wound undulating portions. The wire ends (not shown) may be looped and welded to provide no sharp wire ends at the ends of the stent.

Figure 18:
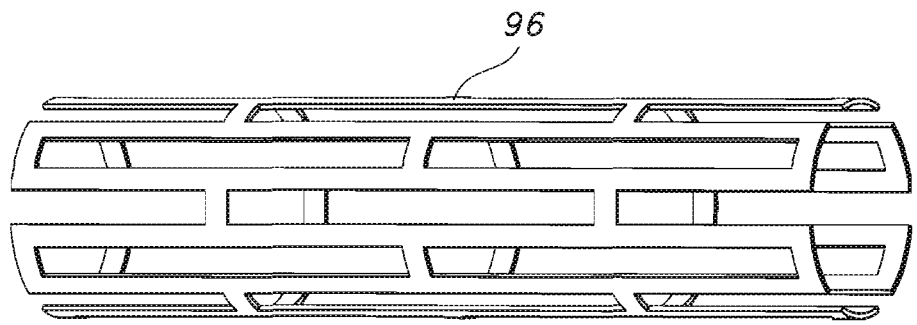
FIG. 18 is a perspective view of a slotted stent for use in the present invention.

A slotted stent 96 may also be useful as stent 20. As depicted in FIG. 18, slotted stent 96 is suitably configured for implantation into a bodily lumen (not shown).

Figure 19:
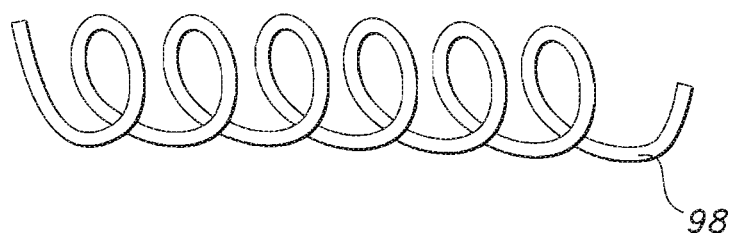
FIG. 19 is a perspective view of a helical coil stent formed of a single wound wire for use in the present invention.
Figure 20:
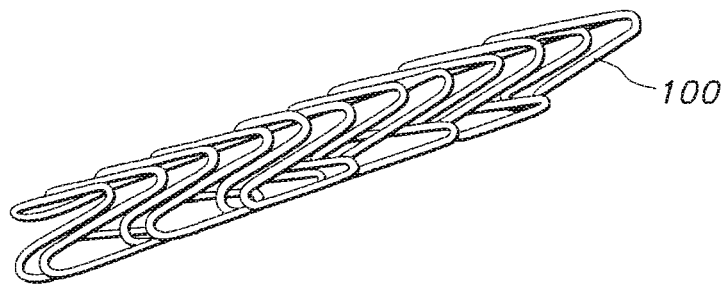
FIG. 20 is a perspective view of a stent having an elongate pre-helically coiled configuration for use in the present invention.

Other useful stents capable of radial expansion are depicted in FIGS. 19 and 20. As depicted in FIG. 19, stent 98 is a helical coil which is capable of achieving a radially expanded state (not shown). Stent 100, as depicted in FIG. 20, has an elongate pre-helically coiled configuration as shown by the waves of non-overlapping undulating windings. These helically coiled or pre-helically stents, commonly referred to as nested stents, are also useful with the practice of one embodiment of the invention.

Figure 44:
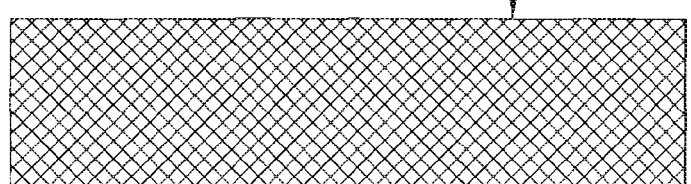
FIG. 44 is a side planar view of a stent for use in the subject invention illustrating a substantially longitudinally straight stent.
Figure 45:
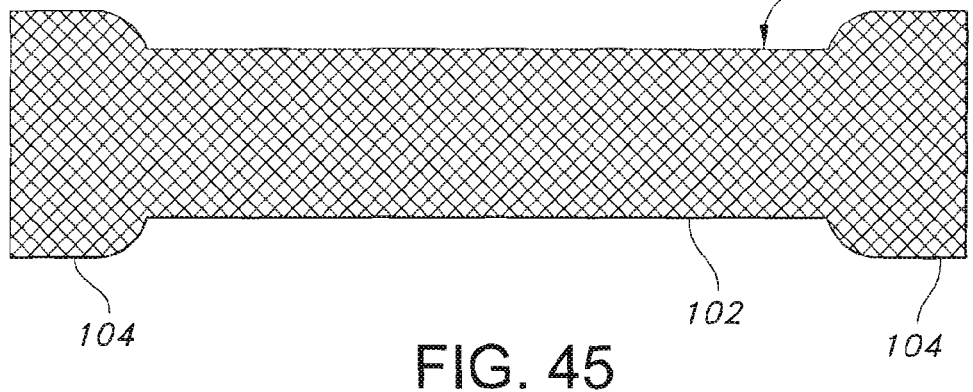
FIG. 45 is a side planar view of a stent illustrating outwardly flared ends according to the present invention.

Further, as depicted in FIG. 44, the stent 20 may have a straight or substantially straight longitudinal portion 102. The present invention, however, is not so limited. For example, the stent 20 may have a varied diameter, such as a flaring or tapering, along a portion or portion of its longitudinal expanse. One non-limiting example of a varied diameter stent 20 is depicted in FIG. 45. The stent 20 of FIG. 45 may include a longitudinal length 102 and one or two flared ends 104. As depicted in FIG. 45, the flared ends 104 are enlarged flared ends having a diameter greater than the diameter of the longitudinal portion 102 of the stent 20. The stent 20, however, is not so limited, and for example the flared ends 104, individually or in combination, may have a smaller diameter than the diameter of the longitudinal portion 102 of the stent 20. Further, the stent 20 may be repositionable, removable and/or reconstrainable, and/or may include multiple interconnected or non-interconnected stents. For example, the stent 20 may include a loop or element, such as a suture loop or element, a polymeric loop or element, metallic loop or element, and combinations thereof which may be accessible to a user or practitioner, for example by the use of forceps, to reposition, remove and/or reconstrain the stent 20 after it has been delivered, partially or totally, to a bodily lumen. Moreover, a loop or element may be integrally formed as part of the stent 20. Further details of useful repositioning, removing and/or reconstraining loops or elements may be found in U.S. patent application Ser. No. 11/341,540, filed Jan. 27, 2006, and entitled "Stent Retrieval Member And Devices And Methods For Retrieving Or Repositioning A Stent", which published as U.S. Patent Application Publication No. 2006/0190075 A1, and in U.S. patent application Ser. No. 11/432,065, filed May 11, 2006, and entitled "Integrated Stent Respostioning And Retrieval Loop", which published as U.S. Patent Application Publication No. 2006/0276887 A1, the contents of both of which are incorporated herein by reference.

In some embodiments, stent may be formed of a metal braid formed of a flat wire. In such embodiments, the flat wire may have a width of between 0.001 inches (0.025 mm) and 0.005 inches (0.13 mm) and a thickness of about 0.001 inches (0.025 mm).

The stent may be coated with a polymeric material. For example, the stent wires may be partially or fully covered with a biologically active material which is elutably disposed with the polymeric material. Further, the polymeric coating may extend over or through the interstitial spaces between the stent wires so as to provide a hollow tubular liner or cover over the interior or the exterior surface of the stent, thereby providing a stent-graft device. The polymeric material may be selected from the group consisting of polyester, polypropylene, polyethylene, polyurethane, polynaphthalene, polytetrafluoroethylene, expanded polytetrafluoroethylene, silicone, and combinations thereof. The covering may be in the form of a tubular structure. The silicone covering may be suitably formed by dip coating the stent. Details of such dip coating may be found in U.S. Pat. No. 5,875,448, the content of which is incorporated herein by reference. The present invention is not limited to forming the silicone film by dip coating, and other techniques, such as spraying, may suitably be used. After applying the silicone coating or film to the stent, the silicone may be cured. Desirably, the curing is low temperature curing, for example from about room temperature to about 90° C. for a short period of time, for example from about 10 minutes or more to about 16 hours. The cured silicone covering may also be sterilized by electronic beam radiation, gamma radiation, ethylene oxide treatment and the like. Further details of the curing and/or sterilization techniques may be found in U.S. Pat. No. 6,099,562, the content of which is incorporated herein by reference. Argon plasma treatment of the cured silicone may also be used. Argon plasma treatment of the cured silicone modifies the surface to the cured silicone to, among other things, make the surface less sticky. The invention, however, is not limited to stent-graft devices having polymeric coatings. The graft portion may suitably be formed from polymeric films, polymeric tapes, polymeric tubes, polymeric sheets and textile materials. Textile material may be woven, knitted, braided and/or filament wound to provide a suitable graft. Various biocompatible polymeric materials may be used as textile materials to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. Moreover, textile materials and stent materials may be co-formed, for example co-braided, to form a stent-graft device.

In some embodiments, stent 20 is a joined or welded stent. In such a stent, elongate wires terminating at an open end of the stent are mated, and adjacently mated wires are secured by welds or other suitable means. For example, the wires may be welded together through use of a welding material or the wires may be fused together without the use of a welding material by means of heating and/or melting. Furthermore, the wires may be mechanically joined, such as, for example, through the use of small-sized or micro-fabricated clamps, crimpable tubes, hypotubes, and the like.

Although the stent may be formed of metals, plastics or other materials, it is preferred that a biocompatible material or construction is used. In particular, the wires or filaments of stents useful in the present invention may be made from a biocompatible material or biocompatible materials. Useful biocompatible materials include, but are not limited to, biocompatible metals, biocompatible alloys, biocompatible polymeric materials, including synthetic biocompatible polymeric materials and bioabsorbable or biodegradable polymeric materials, materials made from or derived from natural sources and combinations thereof. Desirably, the wires are biocompatible metals or alloys made from, for example, nitinol, stainless steel, a cobalt-based alloy such as Elgiloy, platinum, gold, titanium, tantalum, niobium, polymeric materials, and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, silks, and polytetrafluoroethylene. The polymeric materials may further include a metallic, glass, ceramic or carbon constituent or fiber. Useful and non-limiting examples of bioabsorbable or biodegradable polymeric materials include poly(L-lactide) (PLLA), poly(D,L-lactide) (PLA), poly(glycolide) (PGA), poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), polycaprolactone (PCL), polyhydroxybutyrate (PHBT), poly(phosphazene), poly(D,L-lactide-co-caprolactone) (PLA/PCL), poly(glycolide-co-caprolactone) (PGA/PCL), poly(phosphate ester), and the like. Further, stent 20 may include materials made from or derived from natural sources, such as, but not limited to, collagen, elastin, glycosaminoglycan, fibronectin and laminin, keratin, alginate, combinations thereof and the like.

Wires made from polymeric materials also may include radiopaque materials, such as metallic-based powders or ceramic-based powders, particulates or pastes, which may be incorporated into the polymeric material. For example, the radiopaque material may be blended with the polymer composition from which the polymeric wire is formed, and subsequently fashioned into the stent. Alternatively, the radiopaque material may be applied to the surface of the metal or polymer stent. In either embodiment, various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirety by reference. Metallic complexes useful as radiopaque materials also are contemplated.

Stent 20 may be selectively made radiopaque at desired areas along the wire or may be made fully radiopaque, depending on the desired end-product and application. Furthermore, the wires of stent 20 may have an inner core of tantalum, gold, platinum, or iridium, or a combination thereof, and an outer member or layer of nitinol to provide a composite wire for improved radiopacity or visibility.

Alternatively, the stent 20 may also have improved external imaging under magnetic resonance imaging (MRI) and/or ultrasonic visualization techniques. MRI is produced by complex interactions of magnetic and radio frequency fields. Materials for enhancing MRI visibility include, but are not to be limited to, metal particles of gadolinium, iron, cobalt, nickel, dysprosium, dysprosium oxide, platinum, palladium, cobalt-based alloys, iron-based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 20 of the present invention may include ultrasound resonant material, such as but not limited to gold. Other features, which may be included with the stent 20 of the present invention, include radiopaque markers; surface modification for ultrasound, cell growth or therapeutic agent delivery; varying stiffness of the stent or stent components; varying geometry, such as tapering, flaring, bifurcation and the like; varying material; varying geometry of stent components, for example tapered stent filaments; and the like.

Desirably, the wires are made from nitinol, or a composite wire having a central core of platinum and an outer layer of nitinol. Desirably, the inner core of platinum represents about at least 10% of the wire based on the overall cross-sectional percentage. Moreover, the nitinol desirably has not been treated for shape memory such as by heating, shaping and cooling the nitinol at its martensitic and austenitic phases. Further details of suitable composite wires may be found in U.S. Patent Application Publication 2002/0035396 A1, the contents of which are incorporated herein by reference.

The wires of stent 20 may have any suitable diameter. Desirably, the wires are relatively thin and have a diameter of about 0.01 to 0.02 inches.

Moreover, stent 20 may contain any suitable number of wires. Desirably, an even number of wires is used. For example, in some embodiments, stent 20 may contain from about 10 to about 36 wires. Furthermore, stent 20 also may include apertures and/or discontinuities (not shown) along portions of the stent wall.

The stent 20, inner tubular structure 22, and/or exterior tubular structure 10 may have coverings, films, coatings, and the like disposed over, under or throughout or embedding the stent 20. Any suitable covering, film, coating, and the like may be used in combination with the stent 20, the inner tubular structure 22, and/or the exterior tubular structure 10. In particular, the stent 20 may be fully, substantially or partially covered with such a covering, film, coating, and the like on an external and/or internal surface of the stent 20. The covering may be, for example, a graft covering in the form of a hollow, tubular graft structure.

Figure 41:
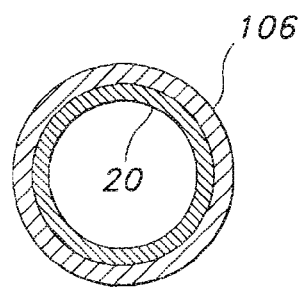
FIG. 41 is a cross-sectional view of the stent of FIG. 40 illustrating an outer graft covering disposed on the stent.
Figure 42:
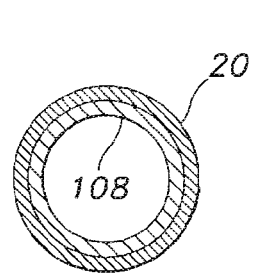
FIG. 42 is a cross-sectional view of the stent of FIG. 40 illustrating an inner graft lining disposed on the stent.
Figure 43:
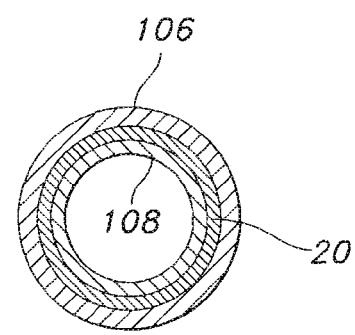
FIG. 43 is a cross-sectional view of the stent of FIG. 40 illustrating an inner graft lining and an outer graft covering disposed on the stent.

For example, as depicted in FIG. 41, the stent 20 may include a covering 106, desirably a polymeric covering, disposed over the longitudinal length or a portion of the longitudinal length of the stent 20. Further, as depicted in FIG. 42, the stent 20 may include a liner 108, desirably a polymeric liner, disposed within the longitudinal length or a portion of the longitudinal length of the stent 20. Moreover, as depicted in FIG. 43, the stent 20 may include both a covering 106 and a liner 108, desirably a polymeric covering and liner which include the same or different polymeric materials, disposed over and within the longitudinal length or a portion of the longitudinal length of the stent 20. The covering and the liner of FIG. 43 may be a unitary film or coating that embeds or partially embeds the stent 20. The covering 106 and/or the liner 108 may be in the form of a tubular structure, for example composed of polymeric material and/or silicone. The covering 106 and/or the liner 108 may also comprise any plastic or polymeric material, desirably a somewhat hard but flexible plastic or polymeric material. The covering 106 and/or the liner 108 may be transparent or translucent, desirably substantially or partially transparent.

The coverings and/or the liner of the present invention may be made from a "textile" material, from a "non-textile" material, or from a combination thereof. As used herein, the term "textile" refers to a material, such as a yarn, that may be knitted, woven, braided, or the like, into a structure, such as a hollow, tubular structure. As used herein, the term "non-textile" refers to a material formed by casting, molding, spinning or extruding techniques to the exclusion of typical textile forming techniques, such as braiding, weaving, knitting, and the like. In particular, the covering 106 and/or the liner 108 may be constructed of any suitable biocompatible materials, such as, but not limited to, polymers and polymeric materials, including fillers such as metals, carbon fibers, glass fibers or ceramics.

Useful covering 106 and/or liner 108 materials include, but are not limited, polyethylene, polypropylene, polyvinyl chloride, polytetrafluoroethylene (PTFE), including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, silicones, and copolymers and combinations thereof.

The coating or coatings may be on the stent 20, components of the stent 20, and combinations thereof. The stent components, in part or in total, may be temporary, for example bioabsorbable, biodegradable, and the like, or may be permanent (i.e., not substantially bioabsorbable or biodegradable), for example the above-described biocompatible metals, alloys and polymers.

Desirably, the stent 20 includes braided polyester filaments, such as PET polyester filaments. Further, in some applications, the stent 20 is desirably embedded in a coating of silicone. Additional details of such desirable stents are described in U.S. Pat. No. 6,162,244, the contents of which are incorporated herein by reference.

When a silicone covering is used, the silicone may be disposed on external surfaces of the stent 20 and/or on internal surfaces of the stent 20. Such a silicone covering may be in the form of a coating or film and may be suitably formed by dip-coating the stent. Details of such dip-coating may be found in U.S. Pat. No. 5,875,448, the contents of which are incorporated herein by reference. Moreover, other techniques, such as spraying, may suitably be used to form the silicone covering. After applying the silicone coating or film to the stent, the silicone may be cured. Desirably, the curing is low temperature curing. For example, the curing desirably occurs from about room temperature to about 90° C. for a short period of time which may be, for example, from about 10 minutes or more to about 16 hours. The cured silicone covering also may be sterilized by electronic beam radiation, gamma radiation ethylene oxide treatment, and the like. Further details of the curing and/or sterilization techniques may be found in U.S. Pat. No. 6,099,562, the contents of which are incorporated herein by reference. Argon plasma treatment of the cured silicone also may be used. Argon plasma treatment of the cured silicone modifies the surface of the cured silicone to, among other things, make the surface less sticky.

Suitable textile materials for use in the present invention may be formed from synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament or spun-types. As is well-known, the type and denier of the yarn chosen may be selected in a manner which forms a prosthesis and, more particularly, a vascular structure having desirable properties.

The yarns for use in textile graft coverings of the present invention may be knitted, woven, or braided in any manner known in the art. The knit may be a circular knit or may be a flat knitted tubular knit. Useful knits include, but are not limited to, a high stretch knit, a locknit knit (which also is referred to as tricot or jersey knit), reverse locknit knits, sharkskin knits, queenscord knits, and velour knits. Useful high stretch, warp-knitted patterns include those with multiple patterns of diagonally shifting yarns, such as certain modified atlas knits which are described in U.S. Pat. No. 6,540,773, the contents of which are incorporated herein by reference. Other useful high-stretch, warp knitted patterns include certain patterns with multiple needle underlap and one needle overlap, such as those patterns described in U.S. Pat. No. 6,554,855 and U.S. Patent Application Publication No. 2003/0204241 A1, the contents of which are incorporated herein by reference. U.S. Pat. No. 5,653,746, the contents of which are incorporated herein by reference, further describes useful knits. Useful braids include, but are not limited to, those described in U.S. Pat. No. 5,653,746, the contents of which are incorporated herein by reference. Useful weaves include, but are not limited to, a plain or regular weave, a basket weave, a twill weave, a satin weave, a velour weave, a circular weave, a flat tubular weave, or the like. Suitable textiles and methods for making the same are further discussed in U.S. application Ser. No. 11/025,571, filed Dec. 29, 2004, the contents of which are incorporated herein by reference.

In some embodiments, stent 20 may be treated with any suitable therapeutic agent. Non-limiting examples of suitable therapeutic agents include the following: anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Suitable stents and materials for stents for use in the present invention include those discussed in U.S. application Ser. No. 11/271,774, filed Nov. 10, 2005, U.S. application Ser. No. 11/365,324, filed Mar. 1, 2006, U.S. Application No. 60/819,422, filed Jul. 7, 2006, U.S. application Ser. No. 11/437,889, filed May 19, 2006, U.S. application Ser. No. 11/437,455, filed May 19, 2006, and U.S. application Ser. No. 11/437,459, filed May 19, 2006, the contents of all of which are incorporated herein by reference.

The stent 20 of the stent delivery systems of the present invention may be delivered to a bodily lumen using any suitable delivery device known in the art. In some embodiments, a wire is used to deliver the stent to a bodily lumen. In other embodiments, a rapid exchange catheter such as the rapid exchange catheter disclosed in U.S. Pat. No. 6,592,549, the full contents of which are incorporated by reference herein, may be used. In still other embodiments, stent delivery may be through an endoscope. In yet other embodiments, a delivery device is employed which includes a fiber optic or a chip which allows visualization of the placement of the stent. In still other embodiments, a balloon catheter may be employed to deliver stent to the bodily lumen. It still other embodiments, stent delivery may be unassisted (i.e., no wire or endoscope is employed). Moreover, stent delivery device may have variable stiffness.

While various embodiments of the present invention are specifically illustrated and/or described herein, it will be appreciated that modifications and variations of the present invention may be effected by those skilled in the art without departing from the spirit and intended scope of the invention.

What is claimed is:

1. A device for delivering a stent to a patient for implantation comprising:
   (i) a first tubular structure having a proximal end, a distal end, and a lumen extending therethrough;
   (ii) a second tubular structure having a proximal end, a distal end, and a lumen extending therethrough;
   (iii) the stent having a proximal end and a distal end;
   (iv) a stent-engaging member;
   (v) a distal tip; and
   (vi) a handle positioned over a portion of the proximal end of the first tubular structure, wherein the handle is funnel-shaped and configured to receive the distal end of the stent therein,
   wherein said stent is disengagedly coupled to the second tubular structure via the stent-engaging member, wherein the second tubular structure is positioned within the first tubular structure and the stent is movable with respect to the first tubular structure, wherein the stent is positioned external to the second tubular structure, wherein the stent-engaging member is positioned between the second tubular structure and the stent, wherein the stent-engaging member is positioned in its entirety internal to the stent, wherein the distal tip is configured to attach to the distal end of the second tubular structure after insertion of the stent into the device, and wherein the stent-engaging member is selected from the group consisting of an annular protuberance, a flat holder, and an anchor.

2. The device of claim 1, wherein the stent is positioned within the first tubular structure.

3. The device of claim 1, wherein the distal end of said first tubular structure is aligned with the distal end of the second tubular structure.

4. The device of claim 1, wherein the stent-engaging member is disengageably attached to the second tubular structure.

5. The device of claim 4, wherein the stent-engaging member is disengageably attached to the stent.

6. The device of claim 1, wherein the second tubular structure comprises the stent-engaging member.

7. The device of claim 1, wherein the first tubular structure comprises a marker.

8. The device of claim 7, wherein the marker is selected from the group consisting of ink, thread and combinations thereof.

9. The device of claim 7, wherein the marker is radiopaque.

10. The device of claim 1, further comprising a second stent-engaging member.

11. The device of claim 1, wherein the distal tip comprises a lock that engages the distal end of the second tubular structure upon the distal tip being inserted into the distal end of the second tubular structure.

12. The device of claim 1, wherein the distal tip comprises a thread that engages the distal end of second tubular structure.

13. The device of claim 1, further comprising a locking clip, wherein the distal tip defines a first slot, the distal end of the second tubular structure defines a second slot, and wherein the locking clip is placed within the first slot and second slot.

14. A stent delivery assembly comprising a device for delivering a stent to a patient for implantation, said device comprising:
   (i) a first tubular structure having a proximal end, a distal end, and a lumen extending therethrough;
   (ii) a second tubular structure having a proximal end, a distal end, and a lumen extending therethrough;
   (iii) the stent having a proximal end and a distal end;
   (iv) a stent-engaging member;
   (v) a distal tip; and
   (vi) a handle positioned over a portion of the proximal end of the first tubular structure, wherein the handle is funnel-shaped and configured to receive the distal end of the stent therein,
   wherein said stent is disengagedly coupled to the second tubular structure via the stent-engaging member, wherein the second tubular structure is positioned within the first tubular structure and the stent is longitudinally movable within the first tubular structure and deployable therefrom, wherein the stent is positioned external to the second tubular structure, wherein the stent-engaging member is positioned between the second tubular structure and the stent, wherein the stent-engaging member is positioned in its entirety internal to the stent, wherein the distal tip is configured to attach to the distal end of the second tubular structure after insertion of the stent into the device, and wherein the stent-engaging member is selected from the group consisting of an annular protuberance, a flat holder, and an anchor.

15. The assembly of claim 14, wherein the distal tip comprises a lock that engages the distal end of the second tubular structure upon the distal tip being inserted into the distal end of the second tubular structure.

16. The assembly of claim 14, wherein the distal tip comprises a thread that engages the distal end of second tubular structure.

17. The assembly of claim 14, further comprising a locking clip, wherein the distal tip defines a first slot, the distal end of the second tubular structure defines a second slot, and wherein the locking clip is placed within the first slot and second slot.

18. A device for delivering a stent to a patient for implantation comprising:
   (i) a first tubular structure having a proximal end, a distal end, and a lumen extending therethrough;
   (ii) a second tubular structure having a proximal end, a distal end, and a lumen extending therethrough;
   (iii) the stent having a proximal end and a distal end;
   (iv) a stent-engaging portion;
   (v) a distal tip; and
   (vi) a handle positioned over a portion of the proximal end of the first tubular structure, wherein the handle is funnel-shaped and configured to receive the distal end of the stent therein,
   wherein said stent is disengagedly coupled to the second tubular structure via the stent-engaging portion, wherein the second tubular structure is positioned within the first tubular structure and the stent is movable with respect to the first tubular structure, wherein the stent-engaging portion is positioned in its entirety internal to the stent, wherein the distal tip is configured to attach to the distal end of the second tubular structure after insertion of the stent into the device, and wherein the stent-engaging portion is part of the second tubular structure itself.

19. The device of claim 18, wherein the stent-engaging portion comprises a barb, a flap, a pattern, a bump, an annular ridge, a tacky layer, a divot, and combinations thereof.

20. The device of claim 18, wherein the distal tip comprises a lock that engages the distal end of the second tubular structure upon the distal tip being inserted into the distal end of the second tubular structure.

21. The device of claim 18, wherein the distal tip comprises a thread that engages the distal end of second tubular structure.

22. The device of claim 18, further comprising a locking clip, wherein the distal tip defines a first slot, the distal end of the second tubular structure defines a second slot, and wherein the locking clip is placed within the first slot and second slot.

* * * * *